United States Patent
Heller

(10) Patent No.: US 7,456,213 B2
(45) Date of Patent: Nov. 25, 2008

(54) PEG-POLY(ORTHO ESTER) GRAFT COPOLYMERS AND PHARMACEUTICAL COMPOSITIONS

(75) Inventor: Jorge Heller, Ashland, OR (US)

(73) Assignee: A.P. Pharma, Inc., Redwood City, CA (US)

( * ) Notice: Subject to any disclaimer, the term of this patent is extended or adjusted under 35 U.S.C. 154(b) by 27 days.

(21) Appl. No.: 11/392,989

(22) Filed: Mar. 28, 2006

(65) Prior Publication Data

US 2006/0235083 A1   Oct. 19, 2006

Related U.S. Application Data

(60) Provisional application No. 60/667,880, filed on Mar. 31, 2005.

(51) Int. Cl.
*A61K 31/335* (2006.01)
*A61K 47/34* (2006.01)

(52) U.S. Cl. .............. 514/452; 424/425; 424/486

(58) Field of Classification Search ............. 514/452, 514/456, 772.1
See application file for complete search history.

(56) References Cited

U.S. PATENT DOCUMENTS 5,939,453 A * 8/1999 Heller et al. ............ 514/452
5,968,543 A * 10/1999 Heller et al. ............ 424/425
2003/0152630 A1   8/2003 Ng et al.

* cited by examiner

*Primary Examiner*—Michael G. Hartley
*Assistant Examiner*—Jagadishwar R Samala
(74) *Attorney, Agent, or Firm*—Foley & Lardner LLP

(57) ABSTRACT

This invention relates to graft copolymer delivery vehicles comprising a polyethyleneglycol-poly(ortho ester), and to controlled release pharmaceutical compositions comprising the delivery vehicle and an active agent. The graft copolymer delivery vehicles may be thermogels graft copolymers. The pharmaceutical compositions may be in the form of a topical, syringable, or injectable formulation for local controlled delivery of the active agent.

8 Claims, No Drawings

PEG-POLY(ORTHO ESTER) GRAFT COPOLYMERS AND PHARMACEUTICAL COMPOSITIONS

RELATED APPLICATIONS

This application claims the benefit of U.S. Provisional Patent Application No. 60/667,880, filed Mar. 31, 2005.

BACKGROUND OF THE INVENTION

Field of the Invention

This invention relates to graft copolymer delivery vehicles comprising a polyethyleneglycol-poly(ortho ester), and to controlled release pharmaceutical compositions comprising the delivery vehicle and an active agent. The graft copolymer delivery vehicles may be thermogels graft copolymers. The pharmaceutical compositions may be in the form of a topical, syringable, or injectable formulation for local controlled delivery of the active agent.

Micellar System for Tumor Targeting

One of the major problems in treating cancer is the difficulty of achieving a sufficient concentration of an anticancer agent in the tumor. This is due to the toxicity, sometimes extreme, of such agents which severely limits the amounts that can be used. However, a major discovery in cancer chemotherapy has been the so-called EPR (enhanced permeation and retention) effect. The EPR effect is based on the observation that tumor vasculature, being newly formed vasculature, has an incompletely formed epithelium and is much more permeable than established older vasculature which is essentially impermeable to large molecules. Further, lymphatic drainage in tumors is very poor thus facilitating retention of anticancer agents delivered to the tumor.

The EPR effect can be used in cancer targeting by using delivery systems containing anticancer drugs that are too large to permeate normal vasculature, but which are small enough to permeate tumor vasculature, and two approaches have been developed. In one approach, a water-soluble polymer is used that contains an anticancer drug chemically bound to the polymer via a hydrolytically labile linkage. Such drug-polymer constructs are injected intravenously and accumulate in the tumors, where they are internalized by the cells via endocytosis and released in the lysosomal compartment of the cell via enzymatic cleavage of the labile bond attaching the drug to the polymer. Two disadvantages of this approach are that, first, nondegradable, water-soluble polymers have been used, and this requires a tedious fractionation of the polymer to assure that the molecular weight of the polymer is below the renal excretion threshold, and, second, the drug must be chemically attached to the polymer, which in effect creates a new drug entity with consequent regulatory hurdles that must be overcome. The use of polymer conjugates in cancer diagnosis and treatment is discussed in R. Duncan et al., "The role of polymer conjugates in the diagnosis and treatment of cancer", S.T.P. Pharma Sciences, 6(4), 237-263 (1996), and an example of an alginate-bioactive agent conjugate is given in Al-Shamkhani et al., U.S. Pat. No. 5,622,718.

An alternate approach has been described. In this approach, an AB or ABA block copolymer is prepared where the B-block is hydrophobic and the A-block is hydrophilic. When such a material is placed in water, it will self-assemble into micelles with a hydrophobic core and a hydrophilic shell surrounding the core. Such micelles have a diameter of about 100 nm, which is large enough that when they are injected intravenously, the micelles can not leave the normal vasculature, but they are small enough to leave the vasculature within tumors. Further, a 100 nm diameter is too small to be recognized by the reticuloendothelial system, thus enhancing micelle lifetime within the blood stream. Additionally, when the hydrophilic block is poly(ethylene glycol), further enhancement of circulation time is noted, as has been observed with "stealth" liposomes. The use of block copolymer micelles is reviewed in G. S. Kwon et al., "Block copolymer micelles as long-circulating drug delivery vehicles", Adv. Drug Delivery Rev., 16, 295-309 (1995).

Thermogelling, biodegradable polymer formulations based on poly(DL-lactic acid-co-glycolic acid)/(poly(ethylene glycol) graft copolymers (PLGA-g-PEG) have been reported for use with in vivo biomedical application. The PLGA/PEG graft copolymer system was reported to be a promising platform for protein and cell-based therapy. See B. Jeong et al., Biomacromolecules 2002, 3, 865-868.

Because PEG is hydrophilic and PLGA is hydrophobic, the PLGA-g-PEG copolymer has a hydrophobic backbone while the PEG-g-PLGA copolymer has a hydrophilic backbone. Therefore, due to the surfactant nature of these polymers, PLGA-g-PEG and PEG-g-PLGA form micelles in water. In these micelles, the hydrophilic PEG forms flexible shells while the hydrophobic PLGA forms the micelle cores.

Thermogels

PLURONIC®, marketed by BASF, is a class of copolymers that are composed of poly(oxyethylene) blocks and poly(oxypropylene) blocks that forms a triblock of poly(oxyethylene)-poly(oxypropylene)-poly(oxyethylene). The triblock copolymers absorb water to form gels or thermogels which exhibit reverse thermogelation behavior. Reverse thermogelation behavior refers to a characteristic of the copolymer that exists as a liquid solution at low temperatures, and reversibly form gels at physiologically relevant temperatures. However, the PLURONIC® system is nonbiodegradable.

U.S. Pat. No. 6,117,949 discloses water soluble biodegradable ABA- or BAB-type triblock polymer that is made up of a major amount of a hydrophobic polymer made of a poly(lactide-co-glycolide) copolymer or poly(lactide) polymer as the A-blocks and a minor amount of a hydrophilic polyethylene glycol polymer B-block, having an overall weight average molecular weight of between about 2000 and 4990, and that possesses reverse thermogelation properties. The triblock copolymer provide a drug delivery system for the parenteral administration of hydrophilic and hydrophobic drugs, peptide and protein drugs, and oligonucleotides.

U.S. Pat. No. 6,004,573 discloses a water soluble biodegradable ABA-type block copolymer made up of a major amount of hydrophobic poly(lactide-co-glycolide) copolymer A-blocks and a minor amount of a hydrophilic polyethylene glycol polymer B-block, having an overall average molecular weight of between about 3100 and 4500, and possesses reverse thermogelation properties. Effective concentrations of the block copolymer and a drug may be uniformly contained in an aqueous phase to form a drug delivery composition. The composition may be administered to a warm-blooded animal as a liquid by parenteral, ocular, topical, transdermal, vaginal, transurethral, rectal, nasal, oral, or aural delivery means and is a gel at body temperature. The composition may also be administered as a gel, and the drug is released at a controlled rate from the gel which biodegrades into non-toxic products. The release rate of the drug may be adjusted by changing various parameters such as hydrophobic/hydrophilic component content, copolymer concentration, molecular weight and polydispersity of the block copolymer. Because the copolymer is amphiphilic it functions to increase the solubility and/or stability of drugs in the composition.

U.S. Pat. No. 5,702,717 discloses a system and method for the parenteral delivery of a drug in a biodegradable polymeric matrix to a warm blooded animal as a liquid with the resultant formation of a gel depot for the controlled release of the drug. The system comprises an injectable biodegradable block copolymeric drug delivery liquid having reverse thermogelation properties. The delivery liquid is an aqueous solution having dissolved or dispersed therein an effective amount of a drug intimately contained in a biodegradable block copolymer matrix. The copolymer has a reverse gelation temperature below the body temperature of the animal to which it is administered and is made up of (i) a hydrophobic A polymer block comprising a member selected from the group consisting of poly($\alpha$-hydroxy acids) and poly(ethylene carbonates) and (ii) a hydrophilic B polymer block comprising a polyethylene glycol.

Delivery of Active Agents

A large of class of active agents such as antibiotics, antiseptics, corticosteroids, anti-neoplastics, and local anesthetics may be administered to the skin or mucous membrane by topical application, or by injection. The active agent may act locally or systemically. Topical delivery may be accomplished through the use of compositions such as ointments, creams, emulsions, solutions, suspensions and the like. Injections for delivery of the active agents include solutions, suspensions and emulsions. All of these preparations have been extensively used for delivery of active agents for years. However, these preparations suffer the disadvantage that they are short-acting and therefore they often have to be administered several times in a day to maintain a therapeutically effective dose level in the blood stream at the sites where the activity/treatment is required.

In recent years, a great deal of progress has been made to develop dosage forms which, after their administration, provide a long-term therapeutic response. These products may be achieved by microencapsulation, such as liposomes, microcapsules, microspheres, microparticles and the like. For this type of dosage forms, the active agents are typically entrapped or encapsulated in microcapsules, liposomes or microparticles which are then introduced into the body via injection or in the form of an implant. The release rate of the active agent from this type of dosage forms is controlled which eliminates the need for frequent dosing. However their manufacture is cumbersome which often results in high costs. In addition, they, in many cases, have low reproducibility and consequently lack of reliability in their release patterns. Furthermore, if an organic solvent is used in the manufacturing process, there could be organic solvent residues in the compositions which may be highly toxic. The use of an organic solvent is also undesirable for environmental and fire hazard reasons.

Interest in synthetic biodegradable polymers for the delivery of therapeutic agents began in the early 1970's with the work of Yolles et al., *Polymer News*, 1, 9-15 (1970) using poly(lactic acid). Since that time, numerous other polymers have been prepared and investigated as bioerodible matrices for the controlled release of active agents. U.S. Pat. Nos. 4,079,038, 4,093,709, 4,131,648, 4,138,344, 4,180,646, 4,304,767, 4,946,931, and 5,968,543 disclose various types of biodegradable or bioerodible polymers which may be used for controlled delivery of active agents. Many of these polymers may appear in the form of a semi-solid. However the semi-solid polymer materials are often too sticky. As a result, the active agents frequently cannot be easily and reliably released from the semi-solid polymer materials.

The polymers used to develop polymer therapeutics may also be separately developed for other biomedical applications that require the polymer be used as a material. Thus, drug release matrices (including microparticles and nanoparticles), hydrogels (including injectable gels and viscous solutions) and hybrid systems (e.g. liposomes with conjugated poly(ethylene glycol) on the outer surface) and devices (including rods, pellets, capsules, films, gels) can be fabricated for tissue or site specific drug delivery. Polymers are also clinically widely used as excipients in drug formulation. Within these three broad application areas: (1) physiologically soluble molecules, (2) materials, and (3) excipients, biomedical polymers provide a broad technology platform for optimizing the efficacy of an active therapeutic drug.

Poly(ortho esters) are known as potential vehicles for sustained release drug delivery. See, for example, Heller, "Poly (Ortho Esters)", *Adv. Polymer Sci.*, 107, 41-92 (1993), and references cited therein, and U.S. Pat. Nos. 4,304,767, 4,946, 931, 4,957,998, and 5,968,543.

U.S. Pat. No. 5,939,453 describes block copolymers prepared from polyethylene glycols and certain poly(ortho esters).

These and other documents referred to in this application are incorporated into this application by reference.

Bioerodible Graft Copolymer Matrix for Controlled Drug Delivery

In AB, ABA, or BAB block copolymers comprising a hydrophilic A block and a hydrophobic B block, the A and B blocks are incompatible and on a microscopic scale will phase-separate. Similarly, as noted above, graft copolymers such as PLGA-g-PEG and PEG-g-PLGA having both hydrophobic and hydrophilic units may also undergo phase separation. This phase separation imparts unique and useful thermal properties to the material.

There is considerable art in the development of graft copolymers. See for example, B. Jeong et al., *Biomacromolecules* 2002, 3, 865-868; B. Jeong et al., *Macromolecules* 2000, 33, 8317-8322; and B. Jeong, et al., *Chem. Comm.* 2001, 1516-1517. The disclosures of these and other documents referred to throughout this application are incorporated herein by reference in their entirety.

However, no graft copolymer systems, including thermogel graft copolymers, have been described where the hydrophobic, bioerodible segment is a poly(ortho ester) comprising the units as described herein.

SUMMARY OF THE INVENTION

One embodiment of the present invention provides graft copolymer delivery vehicle which comprises a polyethyleneglycol (PEG)-poly(ortho ester) ("POE") copolymer. The graft copolymers may be thermogel graft copolymers. The polyethyleneglycol-poly(ortho ester) graft copolymers, in particular, the POE-g-PEG suitable for the invention are represented by Formula L1, Formula L2, Formulae I-VII, and thoses as disclosed herein.

Another embodiment of the present invention provides a controlled release graft copolymer pharmaceutical composition for local controlled delivery of an active agent. The composition comprises an active agent and the graft copolymer delivery vehicle. As referred to herein, the graft copolymers of the present invention may be thermogel graft copolymers, the graft copolymers may be useful as micelles, as matrices for drug delivery systems, and also for tissue engineering applications as known in the art. In a particular embodiment, the graft copolymers are thermogel graft copolymers.

A further embodiment of the present invention provides a thermogel graft copolymer syringable or injectable composition for the controlled delivery of locally acting active agents, in particular local anesthetics and antiemetic agents.

In a first aspect, this invention provides a graft copolymer delivery vehicle, comprising the Formula L1 or Formula L2:

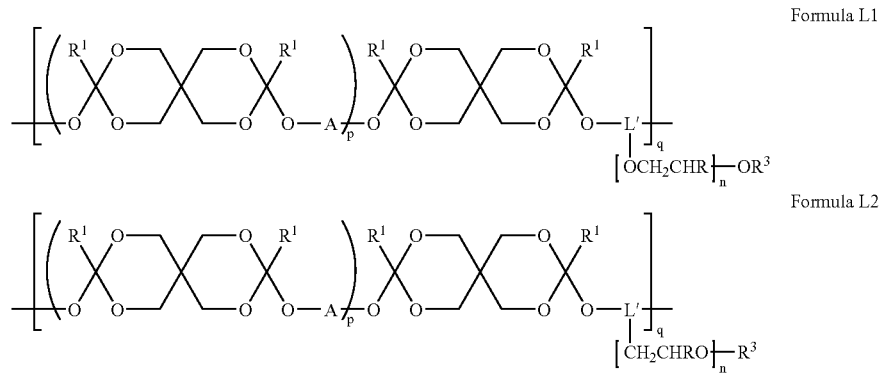

Formula L1

Formula L2 wherein:

L' is linker comprising a backbone chain of 2-10 atoms comprising C, N, O, S, or P optionally interrupted with one or more —C(O)O—, —OC(O)—, —COS—, —SC(O)—, —C(S)O—, —CON—, —CONH—, —CONR'—, —NCO—, —NHCO—, —R'NCO—, —OCO$_2$—, —OCON—, —OCONH—, —NCO$_2$—, —NHCO$_2$—, —OCONR'—, —R'NCO$_2$—, —NCONH—, —NHCON—, —NHCONH—, NR'CONH—, NR'CON—, —NH-CONR'—, —NCONR'—, —NR'CONR'—, —CO—, optionally substituted $C_2$-$C_4$ alkenes, or optionally substituted $C_2$-$C_4$ alkynes, where each R' is independently alkyl, substituted alkyl, aryl or substituted aryl groups;

n is an integer from 2 to 500;

p and q are independently integers from 5 to 100;

$R^1$ is $C_1$-$C_4$ alkyl;

R and $R^3$ are each independently H or $C_1$-$C_4$ alkyl; and each A is independently selected from $R^4$, $R^5$, $R^6$, and $R^7$;

where:

$R^4$ is

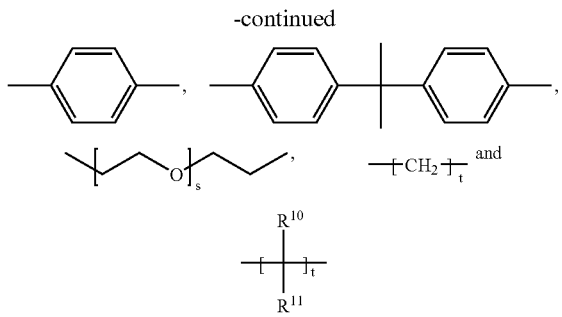

in which:

x is an integer from 0 to 10;

$R^8$ is H or $C_1$-$C_6$ alkyl; and $R^9$ is selected from

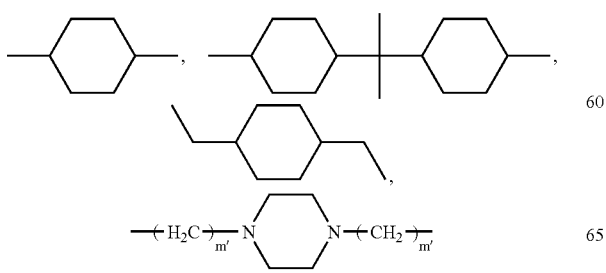

-continued

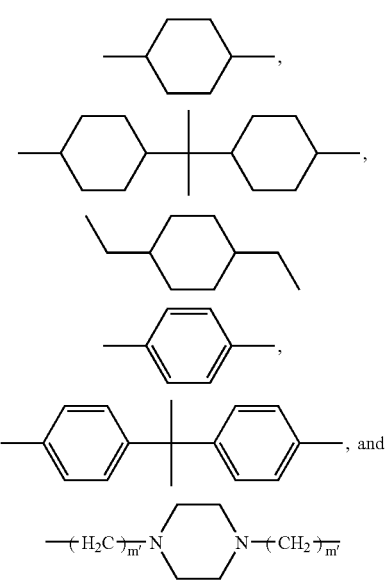

where m' is an integer from 1 to 6, s is an integer from 0 to 30, t is an integer from 1 to 200, and $R^{10}$ and $R^{11}$ are independently H or $C_1$-$C_4$ alkyl;

$R^5$ is selected from:

where m' is an integer from 1 to 6;
R$^6$ is selected from:

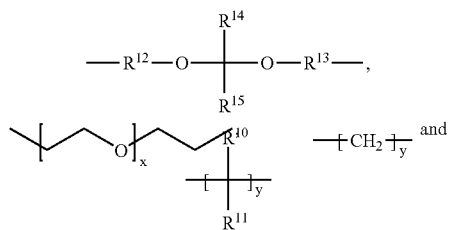

where:
x is an integer from 0 to 30;
y is an integer from 1 to 200;
R$^{10}$ and R$^{11}$ are independently H or C$_1$-C$_4$ alkyl;
R$^{12}$ and R$^{13}$ are independently C$_1$-C$_{12}$ alkylene;
R$^{14}$ is H or C$_1$-C$_6$ alkyl; and R$^{15}$ is C$_1$-C$_6$ alkyl; or R$^{14}$ and R$^{15}$ together are C$_3$-C$_{10}$ alkylene; and R$^7$ is (i) the residue of a diol containing at least one amine functionality incorporated therein, or (ii) the residue of a diol containing at least one functional group independently selected from amide, imide, urea, and urethane groups.

In another aspect, there is provided a graft copolymer of Formula I, Formula II, Formula III or Formula IV:

wherein:
n is an integer from 2 to 500;
p and q are independently integers from 5 to 100;
R$^1$ is C$_1$-C$_4$ alkyl;
R, R$^2$ and R$^3$ are each independently H or C$_1$-C$_4$ alkyl; and
each A is independently selected from R$^4$, R$^5$, R$^6$, and R$^7$;
where:
R$^4$ is

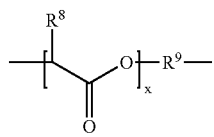

in which:
x is an integer from 0 to 10;
R$^8$ is H or C$_1$-C$_6$ alkyl; and
R$^9$ is selected from Formula I
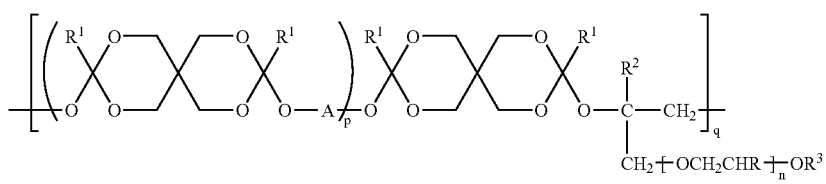

Formula II
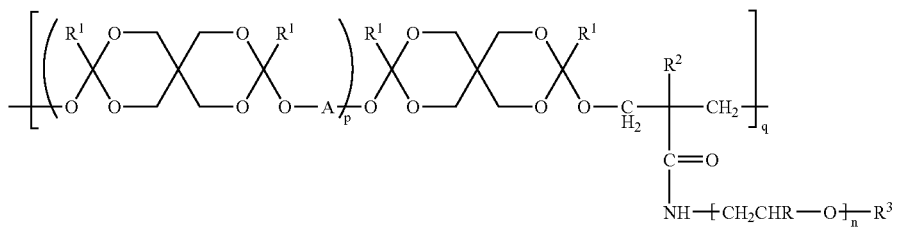

Formula III
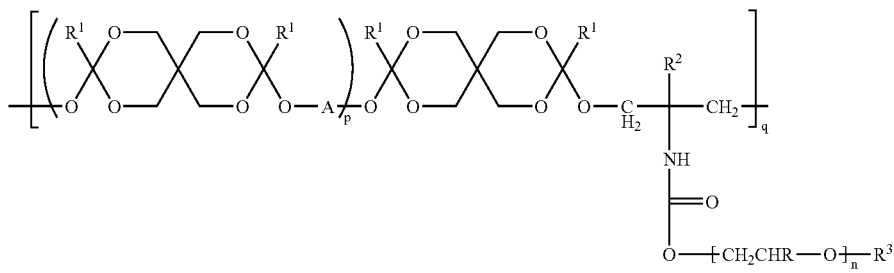

Formula IV
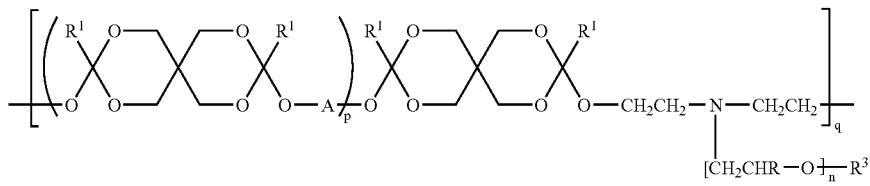

[Chemical structures showing various R groups including cyclohexyl, piperazine, phenyl, and alkyl chains]

$-(H_2C)_{m'}-N\boxed{\phantom{XX}}N-(CH_2)_{m'}-$ $-(CH_2)_t-$ and

[Structure with $R^{10}$ and $R^{11}$ on branching carbon with subscript t]

where m' is an integer from 1 to 6,
s is an integer from 0 to 30,
t is an integer from 1 to 200, and
$R^{10}$ and $R^{11}$ are independently H or $C_1$-$C_4$ alkyl;
$R^5$ is selected from:

[Chemical structures]

, and $-(H_2C)_{m'}-N\boxed{\phantom{XX}}N-(CH_2)_{m'}-$ where m' is an integer from 1 to 6;
$R^6$ is selected from:

$-R^{12}-O-\underset{R^{15}}{\overset{R^{14}}{\mathrm{C}}}-O-R^{13}-$,

[Structure with repeating O unit, subscript x], $-(CH_2)_y-$ and

-continued

[Structure with $R^{10}$ and $R^{11}$, subscript y]

where:
x is an integer from 0 to 30;
y is an integer from 1 to 200;
$R^{10}$ and $R^{11}$ are independently H or $C_1$-$C_4$ alkyl;
$R^{12}$ and $R^{13}$ are independently $C_1$-$C_{12}$ alkylene;
$R^{14}$ is H or $C_1$-$C_6$ alkyl; and $R^{15}$ is $C_1$-$C_6$ alkyl; or $R^{14}$ and $R^{15}$ together are $C_3$-$C_{10}$ alkylene; and $R^7$ is (i) the residue of a diol containing at least one amine functionality incorporated therein, or (ii) the residue of a diol containing at least one functional group independently selected from amide, imide, urea, and urethane groups. In one variation of the copolymer above is a compound of Formula I, Formula II, Formula III or Formula IV where R is H. In another variation of the copolymer, n is an integer from 50 to 250, and p is an integer from 10 to 50. In another variation, $R^1$ is ethyl and $R^2$ is H. In yet another variation, A is $R^5$ and $R^5$ is 1,4-cyclohexanedimethylene. In one particular variation, at least 0.1 mol % of units in which A is $R^4$. In another variation of the above, the copolymer comprises about 0.5-50 mol % of units in which A is $R^4$. In another variation, the copolymer comprises about 1-30 mol % of units in which A is $R^4$. In yet another variation, A is $R^4$ and x is 1 to 2. In one particular variation of the above, $R^8$ is hydrogen or methyl. In another variation, $R^9$ is $-CH_2CH_2OCH_2CH_2OCH_2CH_2-$. In another variation, A is $R^5$ and $R^5$ is 1,4-cyclohexanedimethylene or 1,10-decanylene, and n is an integer from 50 to 250, and p is an integer from 10 to 50.

In one aspect, there is provided a compound of Formula I, Formula II, Formula III or Formula IV where R is H and $R^3$ is methyl. In one variation, n is an integer from 50 to 250, and p is an integer from 10 to 50. In another variation, R' is ethyl. In another variation, A is $R^5$ and $R^5$ is 1,4-cyclohexanedimethylene. In one variation, at least 0.1 mol % of units in which A is $R^4$. In another variation, about 0.5-50 mol % of units in which A is $R^4$. In another variation, about 1-30 mol % of units in which A is $R^4$. In one particular variation of the above, p is 1 to 2. In another variation of the above, $R^8$ is hydrogen or methyl. In another variation, $R^9$ is $-CH_2CH_2OCH_2CH_2OCH_2CH_2-$. In one particular variation, A is $R^5$ and $R^5$ is 1,4-cyclohexanedimethylene or 1,10-decanylene, and n is an integer from 50 to 250, and p is an integer from 10 to 50.

In another aspect, there is provided a process for preparing a copolymer of Formula I, Formula II, Formula III or Formula IV:

Formula I

[Chemical structure of Formula I showing repeating units with $R^1$, $R^2$, $R^3$, A, subscripts p, q, n]

Formula II

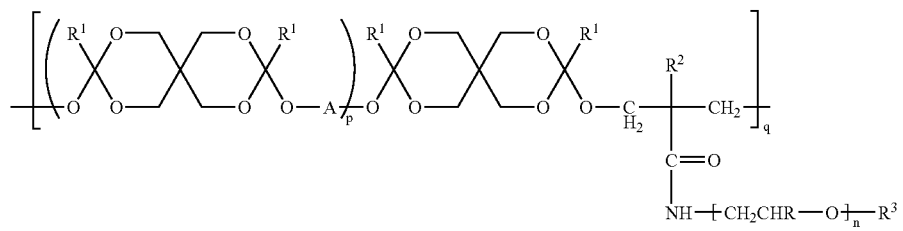

Formula III

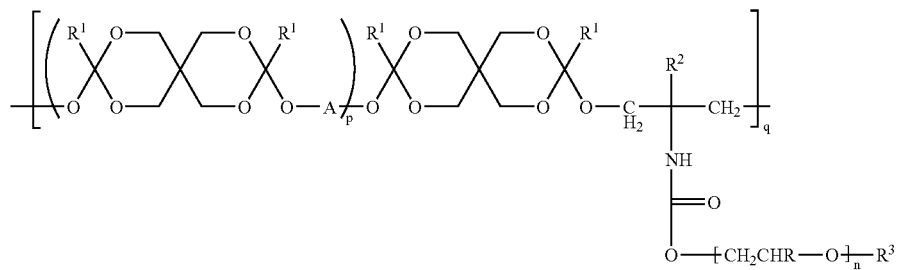

Formula IV

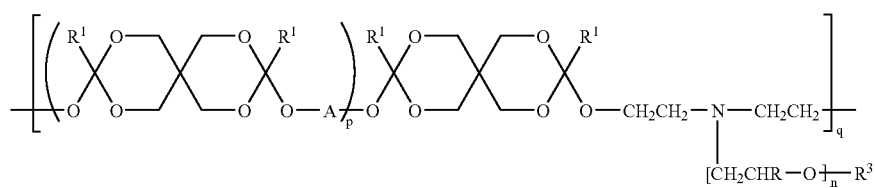

wherein:
n is an integer from 2 to 500;
p and q are independently integers from 5 to 100;
$R^1$ is $C_1$-$C_4$ alkyl;
R, $R^2$ and $R^3$ are each independently H or $C_1$-$C_4$ alkyl; and
each A is independently selected from $R^4$, $R^5$, $R^6$, and $R^7$;
where:
$R^4$ is

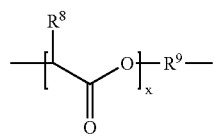

in which:
x is an integer from 0 to 10;
$R^8$ is H or $C_1$-$C_6$ alkyl; and
$R^9$ is selected from

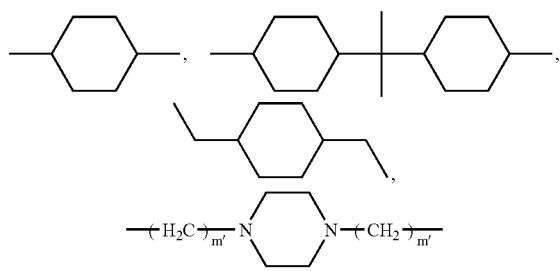

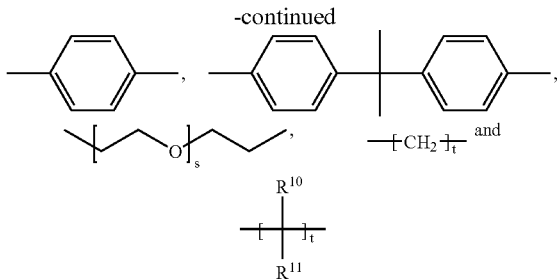

where m' is an integer from 1 to 6,
s is an integer from 0 to 30,
t is an integer from 1 to 200, and
$R^{10}$ and $R^{11}$ are independently H or $C_1$-$C_4$ alkyl;
$R^5$ is selected from:

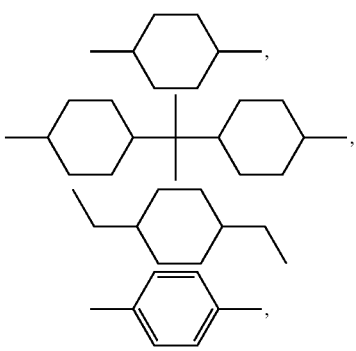

-continued

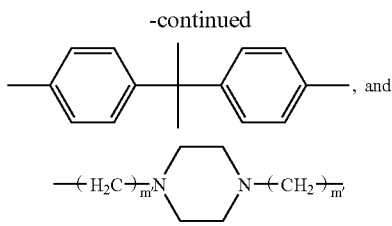
, and where m' is an integer from 1 to 6;

R$^6$ is selected from:

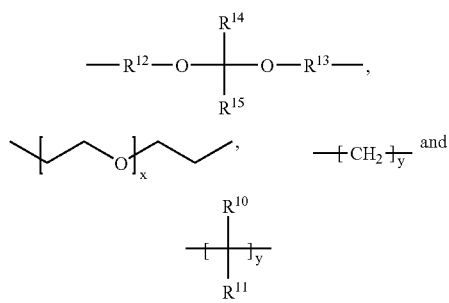

where:

x is an integer from 0 to 30;
y is an integer from 1 to 200;
R$^{10}$ and R$^{11}$ are independently H or C$_1$-C$_4$ alkyl;
R$^{12}$ and R$^{13}$ are independently C$_1$-C$_{12}$ alkylene;
R$^{14}$ is H or C$_1$-C$_6$ alkyl; and R$^{15}$ is C$_1$-C$_6$ alkyl; or R$^{14}$ and R$^{15}$ together are C$_3$-C$_{10}$ alkylene; and R$^7$ is (i) the residue of a diol containing at least one amine functionality incorporated therein, or (ii) the residue of a diol containing at least one functional group independently selected from amide, imide, urea, and urethane groups; the process comprising reacting together a di(ketene acetal), the diol HO-A-OH, and a compound of the Formula Ia, Formula IIa, Formula IIIa or Formula IVa:

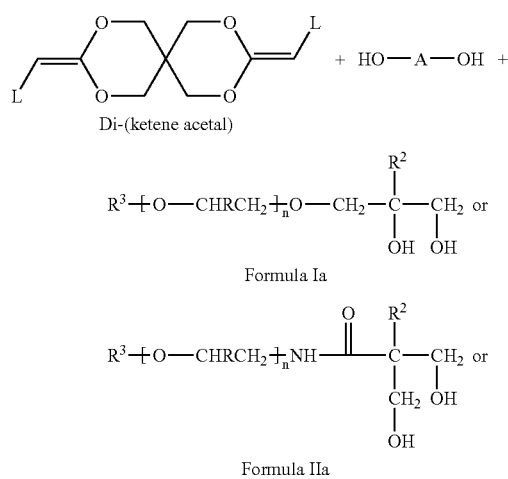

-continued

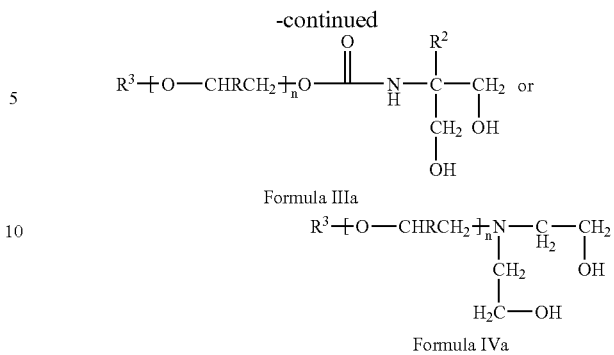

Formula IIIa

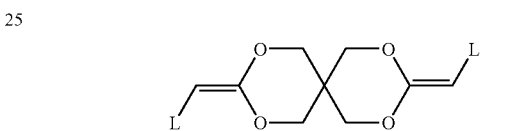

Formula IVa where L is hydrogen or a C$_{1-3}$ alkyl; R, R$^2$ and R$^3$ are each independently H or C$_1$-C$_4$ alkyl with a diol of the formula HO-A-OH that is defined as HO—R$^4$—OH, HO—R$^5$—OH, HO—R$^6$—OH, or HO—R$^7$—OH, or a mixture thereof.

In another aspect, there is provided a copolymer that is the product of a reaction between (a) a di(ketene acetal) of formula:

where L is hydrogen or a C$_1$-C$_3$ alkyl, and (b) at least two polyols or mixture of polyols. In one variation, at least one of the polyols is a polyol having more than two hydroxy functional groups. In another aspect, there is provided a device for orthopedic restoration or tissue regeneration comprising the copolymer of the above.

In yet another aspect, there is provided a pharmaceutical composition comprising (a) an active agent; and (b) as a vehicle, the copolymer described above. In one variation, the fraction of the active agent is from 1% to 60% by weight of the composition. In one variation, the fraction of the active agent is from 5% to 30% by weight of the composition. In another variation, the active agent is selected from anti-infectives, antiseptics, steroids, therapeutic polypeptides, proteins, anti-inflammatory agents, cancer chemotherapeutic agents, narcotics, antiemetics, local anesthetics, antiangiogenic agents, vaccines, antigens, oligonucleotides, RNA, DNA, and antisense oligonucleotides. In one aspect, the active agent is a therapeutic polypeptide. In another aspect, the active agent is a local anesthetic. In another variation, the above pharmaceutical composition further comprising a glucocorticosteroid.

In a particular variation of the above, the active agent is an antiangiogenic agent. In another variation, the active agent is a cancer chemotherapeutic agent. In one variation of the above, the active agent is an antibiotic. In another variation, the active agent is an anti-inflammatory agent. In another aspect, there is provided a method of treating a disease state treatable by controlled release local administration of an active agent, comprising locally administering a therapeutically effective amount of the active agent in the form of the above pharmaceutical composition. In another aspect, there is provided a method of preventing or relieving local pain at a site in a mammal, comprising administering to the site a therapeutically effective amount of a local anesthetic in the form of a pharmaceutically acceptable composition of the above.

In another aspect, there is provided a micellar pharmaceutical composition for the delivery of a hydrophobic or water-insoluble active agent, comprising the active agent physically entrapped within but not covalently bonded to a drug carrier comprising the above copolymer. In one variation of the above, the active agent is an anticancer agent.

In another aspect, there is provided a composition for the sustained release of an active agent, comprising the active agent dispersed in a matrix comprising the above copolymer. In another variation, there is provided a graft copolymer of Formulae L3 or L4:

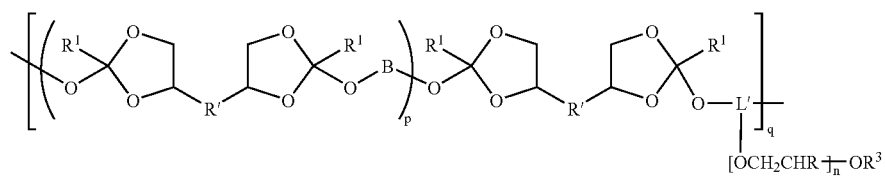

Formula L3

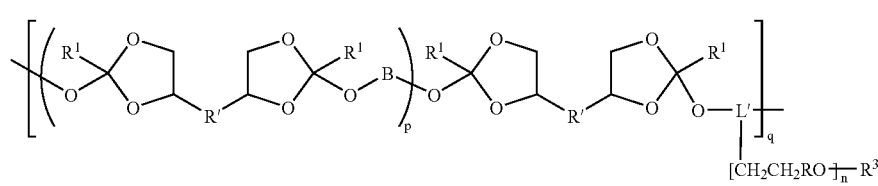

Formula L4 wherein L' is linker comprising a backbone chain of 2-10 atoms comprising C, N, O, S, or P optionally interrupted with one or more —C(O)O—, —OC(O)—, —COS—, —SC(O)—, —C(S)O—, —CON—, —CONH—, —CONR'—, —NCO—, —NHCO—, —R'NCO—, —OCO$_2$—, —OCON—, —OCONH—, —NCO$_2$—, —NHCO$_2$—, —OCONR'—, —R'NCO$_2$—, —NCONH—, —NHCON—, —NHCONH—, NR'CONH—, NR'CON—, —NHCONR'—, —NCONR'—, —NR'CONR'—, —CO—, optionally substituted $C_2$-$C_4$ alkenes, or optionally substituted $C_2$-$C_4$ alkynes, where each R' is independently alkyl, substituted alkyl, aryl or substituted aryl groups; n is an integer from 2 to 500; p and q are independently integers from 5 to 100; $R^1$ is $C_1$-$C_4$ alkyl; R and $R^3$ are each independently H or $C_1$-$C_4$ alkyl; and each A is independently selected from $R^4$, $R^5$, $R^6$, and $R^7$; where:

$R^4$ is

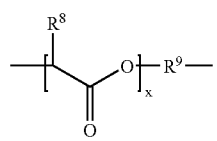

in which:
x is an integer from 0 to 10;
$R^8$ is H or $C_1$-$C_6$ alkyl; and
$R^9$ is selected from

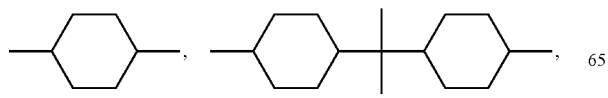

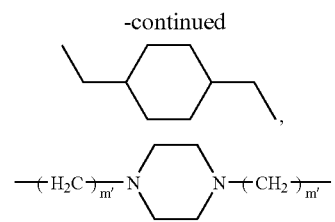

where m' is an integer from 1 to 6,
s is an integer from 0 to 30,
t is an integer from 1 to 200, and
$R^{10}$ and $R^{11}$ are independently H or $C_1$-$C_4$ alkyl;
$R^5$ is selected from:

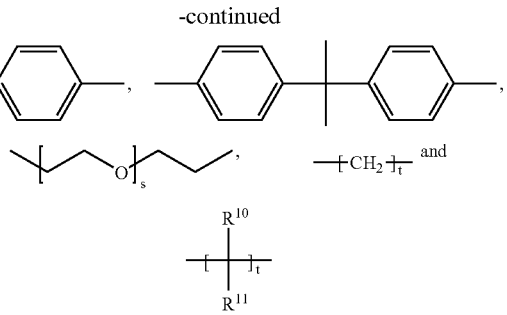

-continued

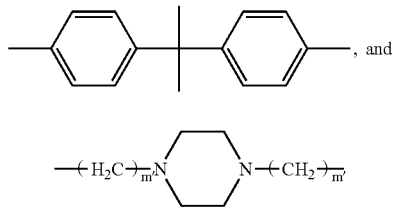, and

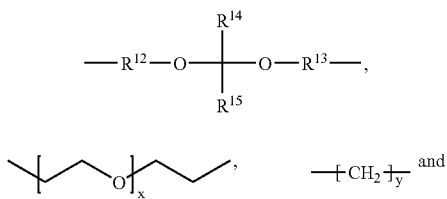

where m' is an integer from 1 to 6;
$R^6$ is selected from:

—$R^{12}$—O—$\underset{R^{15}}{\overset{R^{14}}{C}}$—O—$R^{13}$—,

—$(CH_2CH_2O)_x$—CH₂CH₂—, —$(CH_2)_y$— and

-continued

—$\underset{R^{11}}{\overset{R^{10}}{C}}$—$)_y$ where:
x is an integer from 0 to 30;
y is an integer from 1 to 200;
$R^{10}$ and $R^{11}$ are independently H or $C_1$-$C_4$ alkyl;
$R^{12}$ and $R^{13}$ are independently $C_1$-$C_{12}$ alkylene;
$R^{14}$ is H or $C_1$-$C_6$ alkyl; and $R^{15}$ is $C_1$-$C_6$ alkyl; or $R^{14}$ and $R^{15}$ together are $C_3$-$C_{10}$ alkylene; and $R^7$ is (i) the residue of a diol containing at least one amine functionality incorporated therein, or (ii) the residue of a diol containing at least one functional group independently selected from amide, imide, urea and urethane groups.

In another aspect, there is provided a graft copolymer of Formula IV, Formula V, Formula VI or Formula VII:

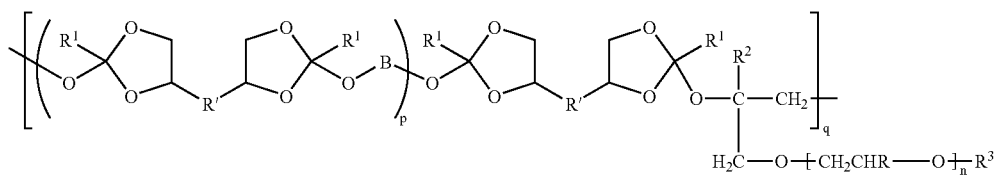

Formula IV

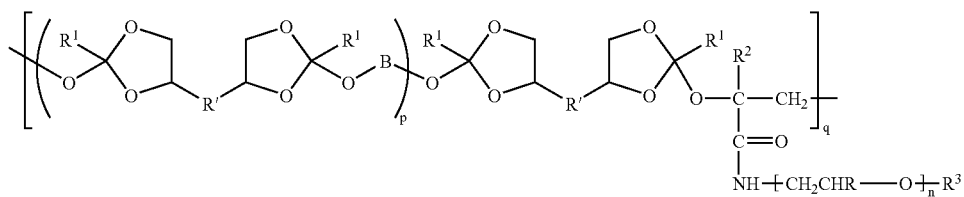

Formula V

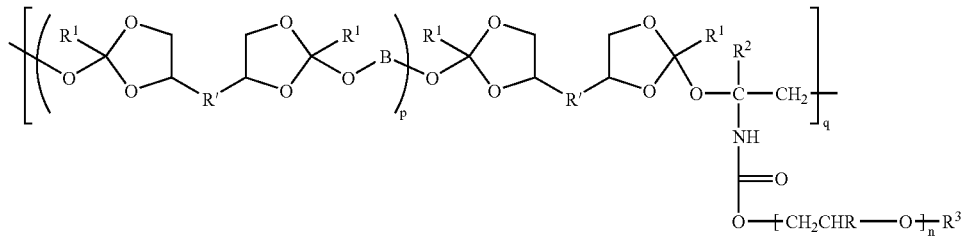

Formula VI

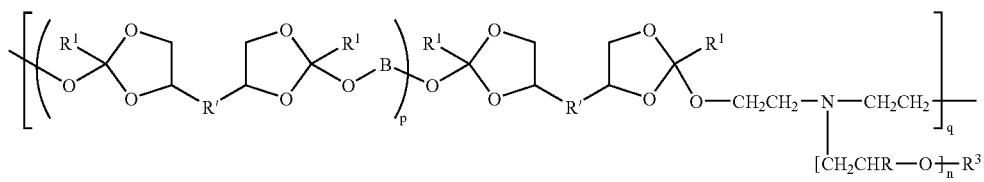

Formula VII where:
n is an integer from 2 to 500;
p and q are independently an integer from 5 to 100;
R' is a bond, —(CH$_2$)$_a$—, or —(CH$_2$)$_b$—O—(CH$_2$)$_c$—;
where a is an integer of 1 to 10, and b and c are independently integers of 1 to 5; R$^1$ is C$_1$-C$_4$ alkyl; R, R$^2$ and R$^3$ are each independently H or C$_1$-C$_4$ alkyl; and each B is independently selected from R$^4$, R$^5$, R$^6$ and R$^7$; where:
R$^4$ is

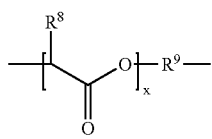

in which:
x is an integer from 0 to 10;
R$^8$ is H or C$_1$-C$_6$ alkyl; and
R$^9$ is selected from

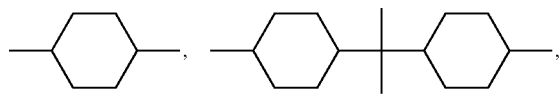

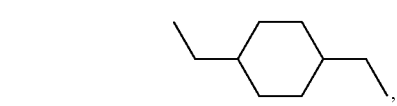

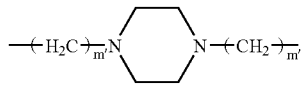

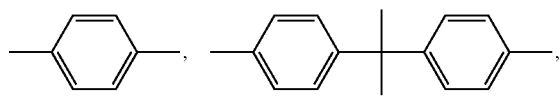

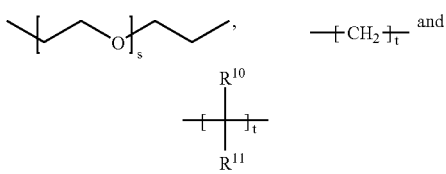

where m is an integer from 1 to 6,
s is an integer from 0 to 30,
t is an integer from 1 to 200, and
R$^{10}$ and R$^{11}$ are independently H or C$_1$-C$_4$ alkyl;
R$^5$ is selected from:

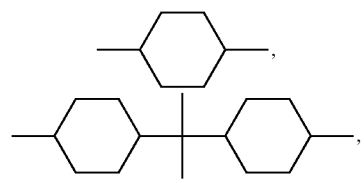

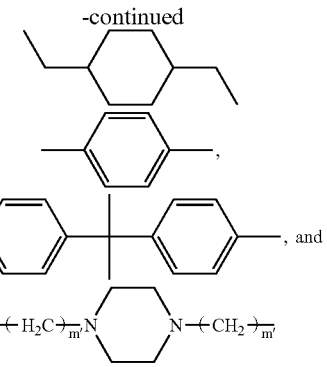

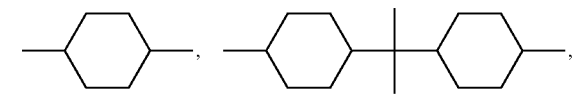

where m' is an integer from 1 to 6;
R$^6$ is selected from:

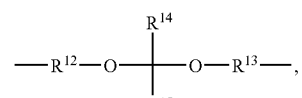

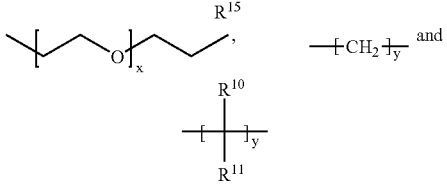

where:
x is an integer from 0 to 30;
y is an integer from 1 to 200;
R$^{10}$ and R$^{11}$ are independently H or C$_1$-C$_4$ alkyl;
R$^{12}$ and R$^{13}$ are independently C$_1$-C$_{12}$ alkylene;
R$^{14}$ is H or C$_1$-C$_6$ alkyl; and R$^{15}$ is C$_1$-C$_6$ alkyl; or R$^{14}$ and R$^{15}$ together are C$_3$-C$_{10}$ alkylene; and R$^7$ is (i) the residue of a diol containing at least one amine functionality incorporated therein, or (ii) the residue of a diol containing at least one functional group independently selected from amide, imide, urea and urethane groups. In one variation, the copolymer is a compound of Formula IV, Formula V, Formula VI or Formula VII where R is H. In another variation, n is an integer from 50 to 250, and p is an integer from 10 to 50. In yet another variation, R$^1$ is ethyl and R$^2$ is H. In another variation, B is R$^5$ and R$^5$ is 1,4-cyclohexanedimethylene. In another variation, at least 0.1 mol % of units in which B is R$^4$. In one variation of the above, about 0.5-50 mol % of units in which B is R$^4$. In another variation, about 1-30 mol % of units in which B is R$^4$. In yet another variation, B is R$^4$ and x is 1 to 2. In another variation, R$^8$ is hydrogen or methyl. In yet another variation, R$^9$ is —CH$_2$CH$_2$OCH$_2$CH$_2$OCH$_2$CH$_2$—. In yet another variation, B is R$^5$ and R$^5$ is 1,4-cyclohexanedimethylene or 1,10-decanylene, n is an integer from 50 to 250, and p is an integer from 10 to 50.

In one aspect, there is provided a process for preparing a copolymer of Formula IV, Formula V, Formula VI or Formula VII:

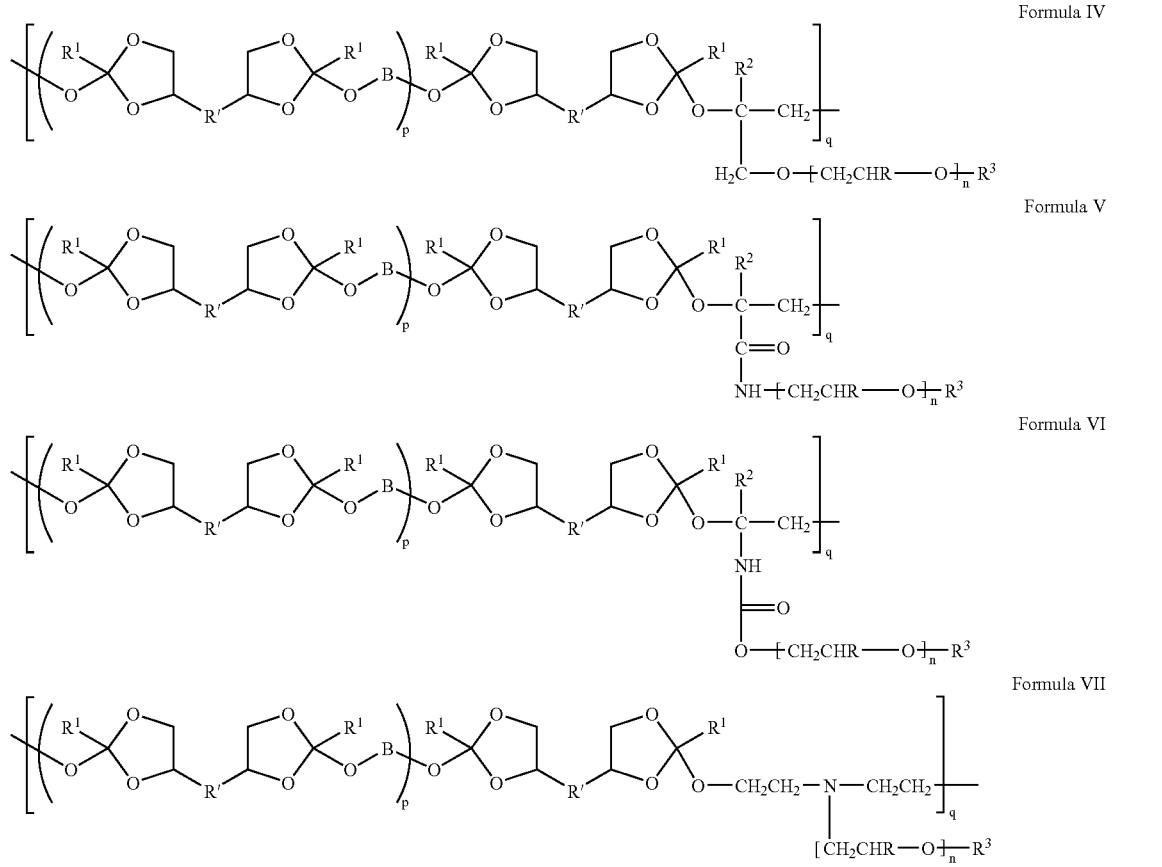

Formula IV

Formula V

Formula VI

Formula VII where:
  n is an integer from 2 to 500;
  p and q are independently an integer from 5 to 100;
  R' is a bond, —(CH$_2$)$_a$—, or —(CH$_2$)$_b$—O—(CH$_2$)$_c$—;
where a is an integer of 1 to 10, and b and c are independently integers of 1 to 5;
  R$^1$ is C$_1$-C$_4$ alkyl;
  R, R$^2$ and R$^3$ are each independently H or C$_1$-C$_4$ alkyl; and
  each B is independently selected from R$^4$, R$^5$, R$^6$, and R$^7$; where:
  R$^4$ is

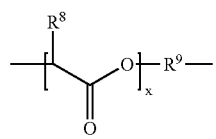

in which:
  x is an integer from 0 to 10;
  R$^8$ is H or C$_1$-C$_6$ alkyl; and
  R$^9$ is selected from

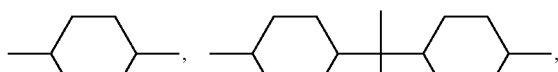

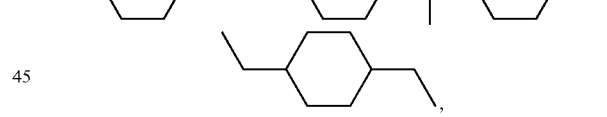

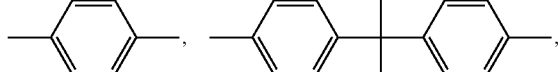

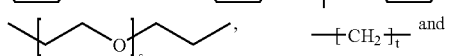

where m' is an integer from 1 to 6,
  s is an integer from 0 to 30,
  t is an integer from 1 to 200, and
  R$^{10}$ and R$^{11}$ are independently H or C$_1$-C$_4$ alkyl;
  R$^5$ is selected from:

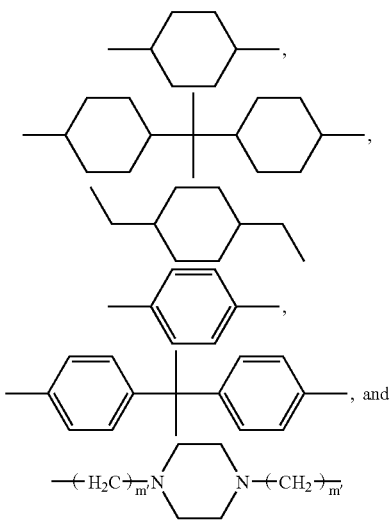

where m' is an integer from 1 to 6;
$R^6$ is selected from:

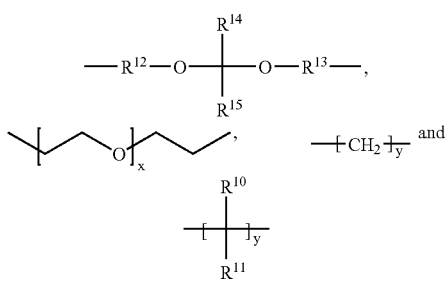

where:
x is an integer from 0 to 30;
y is an integer from 1 to 200;
$R^{10}$ and $R^{11}$ are independently H or $C_1$-$C_4$ alkyl;
$R^{12}$ and $R^{13}$ are independently $C_1$-$C_{12}$ alkylene;
$R^{14}$ is H or $C_1$-$C_6$ alkyl; and $R^{15}$ is $C_1$-$C_6$ alkyl; or $R^{14}$ and $R^{15}$ together are $C_3$-$C_{10}$ alkylene; and $R^7$ is (i) the residue of a diol containing at least one amine functionality incorporated therein, or (ii) the residue of a diol containing at least one functional group independently selected from amide, imide, urea, and urethane groups; the process comprising reacting together a di(ketene acetal), the diol HO—B—OH, and a compound of the Formula IVa, Formula Va, Formula VIa or Formula VIIIa:

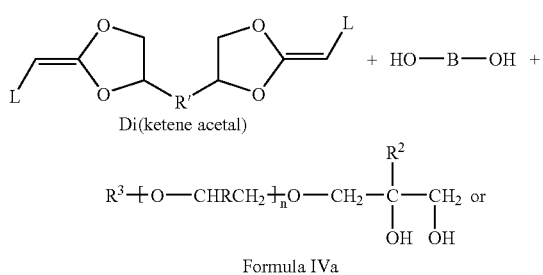

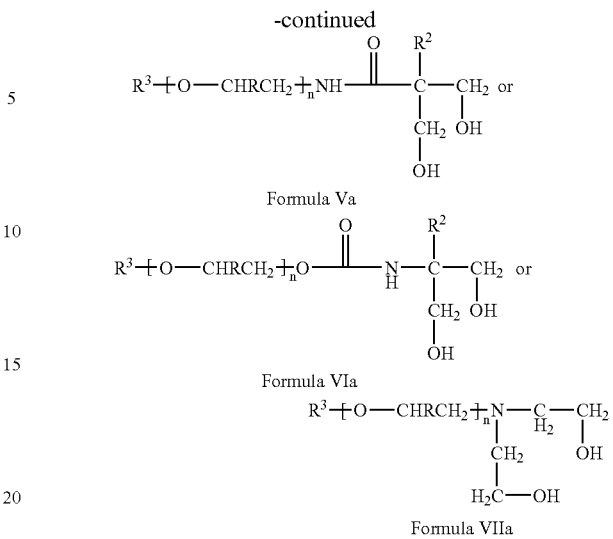

where L is hydrogen or a $C_{1-3}$ alkyl; R, $R^2$ and $R^3$ are each independently H or $C_1$-$C_4$ alkyl; with a diol of the formula HO—B—OH that is defined as HO—$R^4$—OH, HO—$R^5$—OH, HO—$R^6$—OH, or HO—$R^7$—OH, or a mixture thereof.

In one aspect, there is provided a copolymer that is the product of a reaction between (a) a di(ketene acetal) of formula:

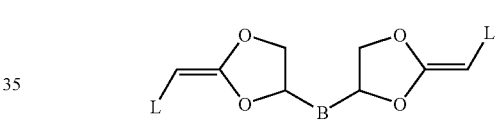

where: L is hydrogen or a $C_1$-$C_3$ alkyl, and (b) at least two polyols or a mixture of polyols. In one variation, at least one of the polyols is a polyol having more than two hydroxy functional groups. In one variation, there is provided a device for orthopedic restoration or tissue regeneration comprising the above copolymer. In another aspect, there is provided a pharmaceutical composition comprising: (a) an active agent; and (b) as a vehicle, the above copolymer. In one variation, the fraction of the active agent is from 1% to 60% by weight of the composition. In another variation, the fraction of the active agent is from 5% to 30% by weight of the composition. In another variation, the active agent is selected from anti-infectives, antiseptics, steroids, therapeutic polypeptides, proteins, anti-inflammatory agents, cancer chemotherapeutic agents, narcotics, antiemetics, local anesthetics, antiangiogenic agents, vaccines, antigens, oligonucleotides, RNA, DNA, and antisense oligonucleotides, and mixtures thereof. Non-exclusive examples of such active agents that may be employed in combination include chemotherapeutic and antiemetic agents. In a particular variation, the active agent is a therapeutic polypeptide. In another variation, the active agent is a local anesthetic selected from the group consisting of bupivacaine, lidocaine, mepivacaine, pyrrocaine and prilocaine. In yet another variation, the above copolymer further comprising a glucocorticosteroid. In another variation, the active agent is an antiangiogenic agent. In yet another variation, the active agent is a cancer chemotherapeutic agent. In yet another variation, the active agent is an antibiotic. In another variation, the active agent is an anti-inflammatory agent.

In one aspect, there is provided a method of treating a disease state treatable by controlled release local administration of an active agent, comprising locally administering a therapeutically effective amount of the active agent in the form of the above pharmaceutical composition. In another aspect, there is provided a method of preventing or relieving local pain at a site in a mammal, comprising administering to the site a therapeutically effective amount of a local anesthetic in the form of a pharmaceutically acceptable composition of the above.

In another aspect, there is provided a micellar pharmaceutical composition for the delivery of a hydrophobic or water-insoluble active agent, comprising the active agent physically entrapped within but not covalently bonded to a drug carrier comprising the copolymer of the above. In one variation, the active agent is an anticancer agent. In another variation of the above, the antiemetic agent is selected from the group consisting of 5-HT$_3$ antagonists, a dopamine antagonists, an anticholinergic agents, a GABA$_B$ receptor agonists, an NK$_1$ receptor antagonists, and a GABA$_A\alpha_2$ and/or $\alpha_3$ receptor agonists. In one variation, the antiemetic agent is a 5-HT$_3$ antagonist. In another variation, the 5-HT$_3$ antagonist is selected from the group consisting of ondansetron, granisetron and tropisetron. In another variation, the composition further comprises a second antiemetic agent to form a combination composition. In one variation, the second antiemetic agent is selected from the group consisting of alpha-2 adrenoreceptor agonists, a dopamine antagonist, an anticholinergic agent, a GABA$_B$ receptor agonist, an NK$_1$ receptor antagonist, and a GABA$_A\alpha_2$ and/or $\alpha_3$ receptor agonist. In another variation, there is provided a composition for the sustained release of an active agent, comprising the active agent dispersed in a matrix comprising the above copolymer.

In another aspect, there is provided a controlled release pharmaceutical composition comprising: (a) an active agent; and (b) as a delivery vehicle, the copolymer delivery vehicle described above.

In another aspect, this invention provides a method of treating a disease state treatable by controlled release local administration of an active agent, in particular treating pain by administration of a local anesthetic, comprising locally administering a therapeutically effective amount of the active agent in the form of the pharmaceutical composition described above.

In yet another aspect, this invention provides a method of treating a disease state treatable by controlled release local administration of an active agent, in particular treating or preventing of mausea and/or emesis by administration of an antiemetic agent, comprising locally administering a therapeutically effective amount of the agent in the form of the pharmaceutical composition described above.

DETAILED DESCRIPTION OF THE INVENTION

Definitions

Unless defined otherwise in this specification, all technical and scientific terms are used herein according to their conventional definitions as they are commonly used and understood by those of ordinary skill in the art of synthetic chemistry, pharmacology and cosmetology.

"Active agent" includes any compound or mixture of compounds which produces a beneficial or useful result. Active agents are distinguishable from such components as vehicles, carriers, diluents, lubricants, binders and other formulating aids, and encapsulating or otherwise protective components. Examples of active agents and their pharmaceutically acceptable salts, are pharmaceutical, agricultural or cosmetic agents. Suitable pharmaceutical agents include locally or systemically acting pharmaceutically active agents which may be administered to a subject by topical or intralesional application (including, for example, applying to abraded skin, lacerations, puncture wounds, etc., as well as into surgical incisions) or by injection, such as subcutaneous, intradermal, intramuscular, intraocular, or intra-articular injection. Examples of these agents include, but not limited to, anti-infectives (including antibiotics, antivirals, fungicides, scabicides or pediculicides), antiseptics (e.g., benzalkonium chloride, benzethonium chloride, chlorhexidine gluconate, mafenide acetate, methylbenzethonium chloride, nitrofurazone, nitromersol and the like), steroids (e.g., estrogens, progestins, androgens, adrenocorticoids, and the like), therapeutic polypeptides (e.g. insulin, erythropoietin, morphogenic proteins such as bone morphogenic protein, and the like), analgesics and anti-inflammatory agents (e.g., aspirin, ibuprofen, naproxen, ketorolac, COX-1 inhibitors, COX-2 inhibitors, and the like), cancer chemotherapeutic agents (e.g., mechlorethamine, cyclophosphamide, fluorouracil, thioguanine, carmustine, lomustine, melphalan, chlorambucil, streptozocin, methotrexate, vincristine, bleomycin, vinblastine, vindesine, dactinomycin, daunorubicin, doxorubicin, tamoxifen, and the like), narcotics (e.g., morphine, meperidine, codeine, and the like), local anesthetics (e.g., the amide- or anilide-type local anesthetics such as bupivacaine, dibucaine, mepivacaine, procaine, lidocaine, tetracaine, and the like), antiemetic agents such as ondansetron, granisetron, tropisetron, metoclopramide, domperidone, scopolamine, and the like, antiangiogenic agents (e.g., combrestatin, contortrostatin, anti-VEGF, and the like), polysaccharides, vaccines, antigens, RNA, DNA and other polynucleotides, antisense oligonucleotides, and the like. The present invention may also be applied to other locally acting active agents, such as astringents, antiperspirants, irritants, rubefacients, vesicants, sclerosing agents, caustics, escharotics, keratolytic agents, sunscreens and a variety of dermatologics including hypopigmenting and antipruritic agents. The term "active agents" further includes biocides such as fungicides, pesticides, and herbicides, plant growth promoters or inhibitors, preservatives, disinfectants, air purifiers and nutrients. Prodrugs of the active agents are included within the scope of the present invention.

"Alkyl" denotes a linear saturated hydrocarbyl having from one to the number of carbon atoms designated, or a branched or cyclic saturated hydrocarbyl having from three to the number of carbon atoms designated (e.g., $C_{1-4}$ alkyl). Examples of alkyl include methyl, ethyl, n-propyl, isopropyl, cyclopropyl, n-butyl, t-butyl, cyclopropylmethyl, and the like. Where an alkyl group is part of a substituted moiety that it further substituted, or where the alkyl group comprises part of a chain or linker, the term "alkyl" may be used interchangeably with the term "alkylene".

"Alkylene" denotes a straight or branched chain divalent, trivalent or tetravalent alkylene radical having from one to the number of carbon atoms designated, or a branched or cyclic saturated cycloalkylenyl having from three to the number of carbon atoms designated (e.g., $C_{1-4}$ alkylenyl, or $C_{3-7}$ cycloalkylenyl), and include, for example 1,2-ethylene, 1,3-propylene, 1,2-propylene, 1,4-butylene, 1,5-pentylene, 1,6-hexylene, 1,2,5-hexylene, 1,3,6-hexylene, 1,7-heptylene, and the like.

"Bioerodible", "biodegradable" and "bioerodibility" refer to the degradation, disassembly or digestion of the polyorthoester by action of a biological environment, including the action of living organisms and most notably at physiological pH and temperature. A principal mechanism for bioerosion of the polyethyleneglycol-poly(ortho ester) of the present invention is hydrolysis of linkages between and within the units of the polyethyleneglycol and/or the poly (ortho ester). Biodegradation of the copolymers forms non-toxic byproducts.

"Graft copolymers" are polymers having a particular type of polymer backbone that contain a graft of another polymer. Thus, a graft copolymer may be prepared by linking together two or more different polymers; or graft copolymers may be prepared by the polymerization of one monomer from initiation sites along the chain of another (backbone) polymer. Graft copolymers of poly(ortho ester)-polyethyleneglycol include polymers having the one or more poly(ortho ester) (POE) as the backbone that is grafted with one or more polyethyleneglycols (PEG) or their derivatives, and polymers having one or more polyethyleneglycols or their derivatives as the backbone that is grafted with one or more poly(ortho esters). As used herein, the phrase poly(ortho ester)-polyethyleneglycol graft copolymer (or PEG/POE, PEG-g-POE, or POE-g-PEG) include all of the above combinations.

"Comprising" is an inclusive term interpreted to mean containing, embracing, covering or including the elements listed following the term, but not excluding other unrecited elements.

"Controlled release", "sustained release", and similar terms are used to denote a mode of active agent delivery that occurs when the active agent is released from the delivery vehicle at an ascertainable and controllable rate over a period of time, rather than dispersed immediately upon application or injection. Controlled or sustained release may extend for hours, days or months, and may vary as a function of numerous factors. For the pharmaceutical composition of the present invention, the rate of release will depend on the type of the excipient selected (when used) and the concentration of the excipient in the composition. Another determinant of the rate of release is the rate of hydrolysis of the linkages between and within the units of the poly(ortho esters) or the rate of hydrolysis of any acid sensitive linkages in the polymer. The rate of hydrolysis in turn may be controlled by the composition of the poly(ortho esters) and the number of hydrolyzable bonds in the poly(ortho esters). Other factors determining the rate of release of an active agent from the present pharmaceutical composition include particle size, solubility of the active agent, acidity of the medium (either internal or external to the matrix) and physical and chemical properties of the active agent in the matrix.

"Delivery vehicle" denotes a composition which has the functions including transporting an active agent to a site of interest, controlling the rate of access to, or release of, the active agent by sequestration or other means, and facilitating the application of the agent to the region where its activity is needed.

"Gel" denotes the semi-solid phase that occurs as the temperature of the copolymer solution or drug delivery liquid is raised to or above the gelation temperature of the copolymer.

"Gelation temperature" denotes the temperature at which the biodegradable copolymer undergoes reverse thermogelation; that is, the temperature below which the copolymer is soluble in water and above which the copolymer undergoes phase transition to increase in viscosity or to form a semisolid gel.

"Matrix" denotes the physical structure of the polyethyleneglycol-poly(ortho ester) or delivery vehicle which essentially retains the active agent in a manner preventing release of the agent until the polyethyleneglycol-poly(ortho ester) erodes or decomposes.

"Polyethyleneglycol-poly(ortho ester)-compatible" refers to the properties of an excipient which, when mixed with the polyethyleneglycol-poly(ortho ester), forms a single phase and does not cause any physical or chemical changes to the polyethyleneglycol-poly(ortho ester).

"Polymer solution," "aqueous solution" and the like, when used in reference to a biodegradable copolymer contained in such solution, shall mean a water based solution having such copolymer dissolved therein at a functional concentration, and maintained at a temperature below the gelation temperature of the copolymer.

"Pro-drug" denotes a pharmacologically inactive or less active form of a compound which must be changed or metabolized in vivo, e.g., by biological fluids or enzymes, by a subject after administration into a pharmacologically active or more active form of the compound in order to produce the desired pharmacological effect. Prodrugs of a compound can be prepared by modifying one or more functional group(s) present in the compound in such a way that the modification(s) may be cleaved in vivo to release the parent compound. Prodrugs include compounds wherein a hydroxy, amino, sulfhydryl, carboxy or carbonyl group in a compound is bonded to any group that can be cleaved in vivo to regenerate the free hydroxyl, amino, sulfhydryl, carboxy or carbonyl group respectively. Examples of prodrugs include, but are not limited to, esters (e.g. acetate, dialkylaminoacetates, formates, phosphates, sulfates and benzoate derivatives) and carbamates of hydroxy functional groups (e.g. N,N-dimethylcarbonyl), esters of carboxyl functional groups (e.g. ethyl esters, morpholinoethanol esters), N-acyl derivatives (e.g. N-acetyl), N-Mannich bases, Schiff bases and enaminones of amino functional groups, oximes, acetals, ketals, and enol esters of ketones and aldehyde functional groups in a compound, and the like.

"Reverse thermogelation" is the phenomena whereby a solution of a copolymer increases in viscosity, and in some circumstances transforms into a semisolid gel, as the temperature of the solution is increased above the gelation temperature of the copolymer. The increase in viscosity may be spontaneous. For the purposes of the invention, the term "gel" includes both the semisolid gel state and the high viscosity state that exists above the gelation temperature. When cooled below the gelation temperature, the gel reverses to reform the lower viscosity solution. This reversal to the lower viscosity solution may be spontaneous. This cycling between the solution and the gel may be repeated ad infinitum because the sol/gel transition does not involve any change in the chemical composition of the polymer system. All interactions to form the gel are physical interactions and do not involve the formation or breaking of covalent bonds.

"Sequestration" is the confinement or retention of an active agent within the internal spaces of a polyethyleneglycol-poly(ortho ester) matrix. Sequestration of an active agent within the matrix may limit the toxic effect of the agent, prolong the time of action of the agent in a controlled manner, permit the release of the agent in a precisely defined location in an organism, or protect unstable agents against the action of the environment.

A "thermogel" as defined herein, is a block or graft copolymer that exists as a solution in water at or about 5 to 25° C., but when the temperature of the thermogel is raised to about body temperature, typically at about 37° C. for humans, the copolymer forms a material that is substantially insoluble in water. Depending on the composition of the thermogel, the transformation of the copolymer may occur spontaneously, may occur in less than about one second, or within about one minute or less. Depending on the composition of the thermogel, the thermogel may exist as a substantially clear solution.

One particular advantage of thermogels is that in the water-soluble form, the thermogels can be administered using a small-bore needle which significantly reduces discomfort during administration. Further, the ability to administer thermogels using a small-bore needle makes thermogels particularly advantageous for ocular applications where the use of large-bore needles, or the implantation of solid devices is more complex and cumbersome, and may lead to difficulties in implantation or operation, and may result in unnecessary tissue damage and the like.

A "therapeutically effective amount" means the amount that, when administered to an animal for treating a disease, is sufficient to effect treatment for that disease.

"Treating" or "treatment" of a disease includes preventing the disease from occurring in an animal that may be predisposed to the disease but does not yet experience or exhibit symptoms of the disease (prophylactic treatment), inhibiting the disease (slowing or arresting its development), providing relief from the symptoms or side-effects of the disease (including palliative treatment), and relieving the disease (causing regression of the disease). For the purposes of this invention, a "disease" includes pain.

A "unit" denotes an individual segment of a polyethyleneglycol-poly(ortho ester) or poly(ortho ester)-polyethyleneglycol graft chain, which, for example, comprises of the residue of an ethyleneglycol molecule or its derivative, a residue of a divinyl ether, and the residue of a polyol.

An "α-hydroxy acid containing" unit denotes a unit where D or D' is $R^4$, i.e. in which the polyol is prepared from an α-hydroxy acid or cyclic diester thereof and a diol of the formula HO—$R^4$—OH. The fraction of the poly(ortho ester)-polyethyleneglycol graft copolymer that is α-hydroxy acid containing units affects the rate of hydrolysis (or bioerodibility) of the poly(ortho ester)-polyethyleneglycol, and in turn, the release rate of the active agent.

An "amine containing" unit denotes a unit where the diol contains at least one amine functionality incorporated therein, which is one of the two types of units where D or D' is $R^7$. The fraction of the poly(ortho ester) that is amine containing units affects the pH-sensitivity of the rate of hydrolysis (or bioerodibilty) of the poly(ortho ester) or graft copolymer containing it, and in turn, the release rate of the active agent. With respect to the individual "amine containing" unit, diols of the formula HO—$R^7$—OH include aliphatic diols of 2 to 20 carbon atoms, preferably 2 to 10 carbon atoms, interrupted by one or two amine groups, and di(hydroxy)- or bis(hydroxyalkyl)-cyclic amines, having from 4 to 20, preferably 4 to 10, carbon or nitrogen atoms between the hydroxy groups; and the amine groups are secondary or, preferably, tertiary, amine groups.

"Hard" and "soft" units denote individual units of the poly(ortho ester), the fractions of which relative to the poly(ortho ester) as a whole determine the mechano-physical state of the poly(orthoester) or graft copolymer containing it. "Hard" units are units where D or D' is $R^5$, "soft" units are units where D or D' is $R^6$.

A "hydrogen bonding" unit denotes a unit where the diol contains at least one functional group independently selected from amide, imide, urea, and urethane groups, which is one of the two types of units where D or D' is $R^7$. The fraction of the poly(ortho ester) that is hydrogen bonding units determines the mechano-physical state of the poly(ortho ester) or graft copolymer containing it.

"Vehicle" and "carrier" denote an ingredient that is included in a composition such as a pharmaceutical or cosmetic preparation for reasons other than a therapeutic or other biological effect. Functions served by vehicles and carriers include transporting an active agent to a site of interest, controlling the rate of access to, or release of, the active agent by sequestration or other means, and facilitating the application of the agent to the region where its activity is needed. Examples of vehicles and carriers include solids such as microparticles, microspheres, rods, and wafers; and semisolids that are dispensable by syringe or the like, or by spreading with a tools such as a spatula.

Ranges given, such as temperatures, times, sizes, and the like, should be considered approximate, unless specifically stated.

Poly(Ortho Ester)-Polyethyleneglycol

The poly(ortho ester)-polyethyleneglycol graft copolymers are of Formulae I-VII, and those disclosed herein. Some of the polymers of the above formulae may be thermogels.

In another aspect, there is provided a composition for the sustained release of an active agent, comprising the active agent dispersed in a matrix comprising the above copolymer.

In one aspect, the structure of the poly(ortho ester)-polyethyleneglycol graft copolymer useful for the present invention, as shown in Formula II is one of a diketene acetal and a diketene acetal residue forming the poly(ortho ester), with each adjacent pairs of the diketene acetal residue being separated by the residue of one polyol, preferably a diol, and the diketene acetal residue is connected to a polyethyleneglycol or a polyethyleneglycol derivative through a linker, wherein the linker is a glycerol derivative.

In another aspect, the structure of the poly(ortho ester)-polyethyleneglycol graft copolymer useful for the present invention, as shown in Formula III is one of a poly(ortho ester) and a diketene acetal residue forming the poly(ortho ester), with each adjacent pairs of the diketene acetal residue being separated by the residue of one polyol, preferably a diol, and the diketene acetal residue is connected to a polyethyleneglycol or a polyethyleneglycol derivative through a linker, wherein the linker is a carboxamide functionalized glycerol derivative.

In the presence of water, the poly(ortho ester)-polyethyleneglycol graft copolymer comprising α-hydroxyacid containing units are hydrolyzed at a body temperature of 37° C. and a physiological pH, to produce the corresponding hydroxyacids. These hydroxyacids then act as acidic catalysts to control the hydrolysis rate of the poly(ortho ester)-polyethyleneglycol graft copolymer without the addition of exogenous acid. When the poly(ortho ester)-polyethyleneglycol graft copolymer is used as a delivery vehicle or matrix entrapping an active agent, the hydrolysis of the poly(ortho ester)-polyethyleneglycol graft copolymer causes release of the active agent.

Substituted ethylene glycol unit or its unsymmetrical derivatives of the formula "—RCH—$CH_2$—O—" or "—$OCH_2$—CHR—" represented in the compounds of the present invention are both intended to be within the scope of the invention. Compounds of the inventions may include various different proportions of the two units, may contain predominantly one unit over the other unit, or may contain a statistical distribution of the units within the polymer, depending on the nature of the R group, the reactants, and the reaction conditions for the preparation of the polymers. By depicting one or the other of the above two units in the formulae of the invention, it is understood for the purpose of the present invention that the compounds or polymers may comprise only one of the two units, different ratios of the two units, a statistical distribution of the two units, or predominantly one unit over the other unit. In a particular preferred aspect, R is hydrogen.

Preferred poly(ortho ester)-polyethyleneglycol graft copolymers are those where:

the poly(ortho ester)-polyethyleneglycol graft copolymer has a molecular weight of 1,000 to 20,000, preferably 1,000 to 10,000, more preferably 1,000 to 8,000;

m is an integer from 2 to 500;
u is an integer from 3 to 100;
$R^0$ is H;
$R^1$ is methyl;
R is hydrogen;
$R^3$ is $C_1$-$C_4$ alkyl; and
D and D' are each independently selected from $R^4$, $R^5$, $R^6$, and $R^7$; where:
$R^4$ is

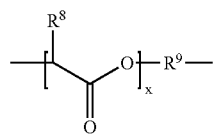

in which:
x is an integer from 0 to 10;
$R^8$ is H or $C_1$-$C_6$ alkyl; and
$R^9$ is selected from

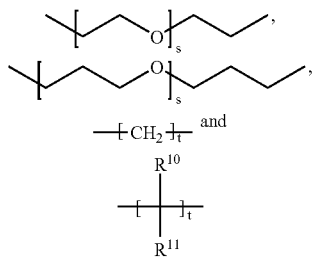

where s is an integer from 0 to 10, especially from 1 to 4, t is an integer from 2 to 50, especially from 2 to 10;

$R^{10}$ and $R^{11}$ are H; and $R^7$ is the residue of a diol of 2 to 20 carbon atoms, preferably 20 to 10 carbon atoms, containing at one or two amine, amide, imide, urea, and urethane groups.

Preferably, the proportion of units in which D and D' is $R^4$ is 0.01-50 mol %, preferably 0.05-30 mol %, more preferably 0.1-25 mol %;

the proportion of units in which D and D' is $R^9$ is less than 20%, preferably less than 10%, especially less than 5%, and the proportion of units in which D and D' is $R^7$ is less than 20%, preferably less than 10%, especially less than 5%.

While the presence of any of these preferences results in a poly(ortho ester)-polyethyleneglycol thermogel graft copolymer that is more preferred than the same poly(ortho ester)-polyethyleneglycol thermogel graft copolymer in which the preference is not met, the preferences are generally independent, and poly(ortho ester)-polyethyleneglycol graft copolymers in which a greater number of preferences is met will generally result in a poly(ortho ester)-polyethyleneglycol thermogel graft copolymer that is more preferred than that in which a lesser number of preferences is met.

Preparation of the Poly(Ortho Ester)-Polyethyleneglycol Graft Copolymer

The poly(ortho ester)-polyethyleneglycol graft copolymer may be prepared according to the methods known in the art, for example, as described in *Contemporary Polymer Chemistry*, H. R. Allcock and F. W. Lampe, Prentice Hall, Inc. Englewood Cliffs, N.J. 07632, 1981, and references cited herein.

For example, the poly(ortho ester)-polyethyleneglycol graft copolymer of Formula II may be prepared by the reaction of a diketene acetal of Formula IIa. In one particular aspect of the invention, a particular compound of the diketene acetal of Formula IIa may be obtained commercially or may be made by any suitable means known in the art. For example, depending on the nature of the variable D, a commercially-obtained amino vinyl ether may be combined with methyl esters to provide the diketene acetal of Formula IIa. See U.S. Patent Publication No. 2002/0082362 A1 to Brocchini et al. Similarly, the hydroxy vinyl ether compound is commercially available, and may be used to make poly(ortho ester) polymers with ester moieties in the main chain. The methyl esters may comprise, for example, esters such as malonates, imines such as iminodiacetates, and other compounds known in the art. In one variation, symmetric, achiral methyl esters may be used as the synthetic precursors.

The polymerization reaction of the diketene acetals with the compound of formula HO-D'-OH and the compound of Formula IIc may be carried out in a solventless system, although preferably the reaction takes place in the presence of an organic solvent selected from aliphatic or aromatic hydrocarbons, which may be optionally halogenated, ethers (including cyclic ethers), dialkylsulfoxides and alcohols (preferably sterically hindered alcohols, for example secondary or tertiary alcohols), or mixtures of solvents therein. Preferred solvents include tetrahydrofuran (THF), dichloromethane, and toluene. A particularly preferred solvent is toluene.

The polymerization of the diol HO-D'-OH with the compound of Formula IIa is generally carried out in the presence of a suitable catalyst such as a catalyst for acid-catalysis, for example, hydrochloric acid, sulfuric acid, phosphoric acid, p-toluenesulfonic acid, methanesulfonic acid, acetic acid, n-butyric acid, trifluoroacetic acid or oxalic acid. A preferred catalyst is p-toluene sulfonic acid (p-TSA). Similarly, the polymerization of the diketene acetal of Formula IIb with the compound of Formula Ic may also be carried out under the similar conditions described above to afford the desired poly (ortho ester)-polyethyleneglycol graft copolymer of Formula II.

The polymerization may be conducted at a temperature of −10° C.-200° C., preferably 20° C.-120° C., most preferably between about 25° C. and 60° C.

In one aspect of the invention, the poly(ortho ester)-polyethyleneglycol graft copolymer may be prepared using a mixture of the two types of the diols of the formula HO-D'-OH or the formula HO-D-OH, the mixture is formed with selected proportions based on the desired characteristics of the poly (ortho ester)-polyethyleneglycol graft copolymer. The use of increasing amounts of diols in which D or D' is $R^4$ increases the bioerodibility of the poly(ortho ester)-polyethyleneglycol, and the use of such diols in which $R^9$ is a polyethyleneoxide moiety or an alkane increases the softness of the polymer; the use of increasing amounts of diols in which D or D' is $R^5$ increases the hardness of the poly(ortho ester)-polyethyleneglycol (and is therefore not generally desirable, though it may be useful in special circumstances); and the use of diols in which D or D' is $R^6$ increases the softness of the poly(ortho ester)-polyethyleneglycol, especially when these diols are low molecular weight polyethylene glycols or aliphatic diols. The use of diols in which D or D' is $R^7$ also generally increases the hardness of the poly(ortho ester)-polyethyleneglycol because of the hydrogen bonding between adjacent chains of the poly(ortho ester)-polyethyleneglycol, and may or may not be desirable depending on the other diols used.

The diols of the formulae HO—$R^4$—OH, HO—$R^5$—OH, HO—$R^6$—OH, and HO—$R^7$—OH are prepared according to methods known in the art, and as described, for example, in U.S. Pat. Nos. 4,549,010 and 5,968,543. Some of the diols are commercially available. The diol of the formula HO—$R^4$—OH that comprises a poly(ortho ester) or poly(ortho ester)-polyethyleneglycol moiety may be prepared by reacting a diol of the formula HO—$R^9$—OH with between 0.5 and 10 molar equivalents of a cyclic diester of an α-hydroxy acid, such as lactide or glycolide, and allowing the reaction to proceed at 100-200° C. for about 12 hours to about 48 hours. Although particular solvents are not required for this reaction, organic solvents such as dimethylacetamide, dimethyl sulfoxide, dimethylformamide, acetonitrile, pyrrolidone, tetrahydrofuran, and methylbutyl ether may be used.

The preparation of diols, in particular the diol of the formula HO—$R^6$—OH is generally disclosed in Heller et al., *J. Polymer Sci., Polymer Letters Ed.* 18:293-297 (1980), by reacting an appropriate diketene acetal with an excess of an appropriate diol. Diols of the formula HO—$R^7$—OH include diols where $R^7$ is R'CONR"R' (amide), R'CONR"COR' (imide), R'NR"CONR"R' (urea), and R'OCONR"R' (urethane), where each R' is independently an aliphatic, aromatic, or aromatic/aliphatic straight or branched chain hydrocarbyl, especially a straight or branched chain alkyl of 2 to 22 carbon atoms, especially 2 to 10 carbon atoms, and more especially 2 to 5 carbon atoms, and R" is hydrogen or $C_{1-6}$ alkyl, especially hydrogen or methyl, more especially hydrogen.

Some representative diols of the formula HO—$R^7$—OH include N,N'-bis-(2-hydroxyethyl)-terephthalamide, N,N'-bis-(2-hydroxyethyl)pyromellitic diimide, 1,1'-methylenedi (p-phenylene)-bis-[3-(2-hydroxyethyl)urea], N,N'-bis-(2-hydroxyethyl)oxamide, 1,3-bis(2-hydroxyethyl)urea, 3-hydroxy-N-(2-hydroxyethyl)propionamide, 4-hydroxy-N-(3-hydroxypropyl)butyramide, and bis(2-hydroxyethyl)ethylenedicarbamate. These diols are known to the art in reported syntheses and may be commercially available. Representative diols of the formula HO—$(CH_2)_n$—NHCO—$(CH_2)_m$—OH, where n is an integer of 2 to 6 and m is an integer of 2 to 5, are made by the reaction of 2-aminoethanol, 3-aminopropanol, 4-aminobutanol, 5-aminopentanol, or 6-aminohexanol with β-propiolactone, γ-butyrolactone, δ-valerolactone, or ε-caprolactone. Representative diols of the formula HO—$(CH_2)_n$—NHCOO—$(CH_2)_m$—OH where n and m are each integers of 2 to 6 are made by the reaction of the same aminoalcohols just mentioned with cyclic carbonates of the formula

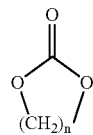

such as ethylene carbonate. Bis-amide diols of the formula HO-A-NHCO—B—CONH-A-OH are prepared by the reaction of a diacid, optionally in activated form, such as the diacyldihalide, with two equivalents of a hydroxy-amine (or amino alcohol). Other methods of preparation of the diols of the formula HO—$R^7$—OH are known in the art.

Once made, the diol of the formula HO—$R^4$—OH and the diol(s) of the formulae HO—$R^5$—OH, HO—$R^6$—OH, and HO—$R^7$—OH in the desired proportions are mixed with the diketene acetal of Formula Ia, in a slightly less than 1:1 (e.g. 0.5:1-0.9:1) ratio of total number of moles of diketene acetal to total number of moles of diols, in a suitable solvent at ambient temperature. The condensation reaction between the diketene acetal and the diols is carried out under conditions which are described in, for example, U.S. Pat. Nos. 4,304, 767, 4,549,010, and 5,968,543, and are well known to those skilled in the art; and will also be readily apparent from the structures of the reactants themselves. Suitable solvents are aprotic solvents, such as dimethylacetamide, dimethyl sulfoxide, dimethylformamide, acetonitrile, acetone, ethyl acetate, pyrrolidone, tetrahydrofuran, and methylbutyl ether, and the like. Catalysts are required for this reaction. Suitable catalysts are iodine in pyridine, p-toluenesulfonic acid; salicylic acid, Lewis acids (such as boron trichloride, boron trifluoride, boron trichloride etherate, boron trifluoride etherate, stannic oxychloride, phosphorous oxychloride, zinc chloride, phosphorus pentachloride, antimony pentafluoride, stannous octoate, stannic chloride, diethyl zinc, and mixtures thereof); and Brønsted acid catalysts (such as polyphosphoric acid, crosslinked polystyrene sulfonic acid, acidic silica gel, and mixtures thereof). A typical amount of catalyst used is about 0.2% by weight relative to the diketene acetal. Smaller or larger amounts can also be used, such as 0.005% to about 2.0% by weight relative to the diketene acetal. Once the reaction is complete, the reaction may be worked up and the product is isolated using the standard methods known in the art. For example, the reaction mixture is allowed to cool and concentrated by rotoevaporation under vacuum. The concentrated mixture may be further dried under vacuum at an elevated temperature.

The poly(ortho ester)-polyethyleneglycols may also be prepared by reaction of the diketene acetal with the chosen diol(s) under similar reaction conditions, but in the presence of a "chain stopper" (a reagent that terminates poly(ortho ester) chain formation). Suitable chain stoppers are $C_{5-20}$ alkanols, especially $C_{10-20}$ alkanols. The chain stopper is preferably present in from 1-20 mol % based on the diketene acetal. The poly(ortho ester)-polyethyleneglycols thus prepared have low molecular weights with a lower molecular weight dispersion than those prepared by the reaction of the diketene acetals with only diols, and are therefore especially suitable for this invention.

Most of the starting materials are commercially available, for example, from Aldrich Chemical Company (Milwaukee, Wis.) and from Abitec Corporation (Columbus, Ohio), LIPO Chemicals Inc. (Paterson, N.J.), and Jarchem Industries, Inc. (Newark, N.J.).

Suitable reaction conditions for the formation of the copolymers are those conditions well known for the formation of poly(ortho ester)s (POE). Typically, the reaction takes place in a polar aprotic solvent, such as those solvents mentioned previously for the preparation of the α-hydroxy acid containing diols, and ethers, especially THF. A catalyst may be used if desired or necessary, and may be selected from those catalysts known to the art for the formation of poly (ortho ester)s. Suitable such catalysts include iodine/pyridine, strong acids such as p-toluenesulfonic acid; Lewis acids, such as boron trichloride etherate, boron trifluoride etherate, tin oxychloride, phosphorus oxychloride, zinc chloride, phosphorus pentafluoride, antimony pentafluoride, stannic chloride, and the like; and Brønsted acids, such as polyphosphoric acid, polystyrenesulfonic acid, and the like. A particularly suitable catalyst is PTSA. A typical amount of catalyst used is about 0.2% by weight relative to the di-vinyl ether, though quantities between 0.005% and 2% may be used.

The bioerodibility of a graft copolymer of this invention is determined by two factors: first, the extent to which the copolymer will dissolve/become suspended intact in an aqueous medium, the solubility of the copolymer; and second, the extent to which the copolymer, or, to be more precise, the PA polymer, will degrade in the environment to which it is exposed. The speed of degradation of the PA of the copolymer in an aqueous environment is determined by the hydrophilicity of the copolymer and by the proportion of α-hydroxy acid ester groups, if present, with greater bioerodibility being achieved by inclusion of a greater proportion of diols of the formula HO—R—OH in the diol mixture used to form the PA polymers.

Uses of the Graft Copolymers of this Invention

While the graft copolymers of this invention will find utility in any of the uses for which biodegradable polymers are useful, including such uses as vehicles for the sustained release of active agents, and the like, they will also find particular utility in applications where their nature as graft copolymers having both hydrophobic and hydrophilic polymers confers a special benefit, and these uses will be addressed in greater detail, since a person of ordinary skill in the art will be well acquainted with the uses of biodegradable polymers and will have no difficulty, having regard to the skill of the art and this disclosure, in adapting the graft copolymers of this invention to such uses.

Micellar System for Tumor Targeting

Polymers useful as micellar delivery systems can be prepared by forming graft copolymers comprising a hydrophilic poly(ethylene glycol) and a hydrophobic poly(ortho esters). When such graft copolymers are placed in water, in which the poly(ethylene glycol) is soluble and the poly(ortho ester) is insoluble, the copolymer chains will spontaneously self-aggregate to form micellar structures. The hydrodynamic diameter of such micelles, which may be determined by methods such as dynamic light scattering, will be in the order of 10-30 nm. As may be determined by methods such as static light scattering, such micelles will contain several hundred polymer chains. The micelles will undergo a secondary, reversible association, giving particles of an average diameter of about 100 nm. While such micelles are too large to be excreted by the kidneys, individual copolymers are not. Further, since the poly(orthoesters) segments can be made to be biodegradable, facile renal excretion will take place.

The major utility of such micellar systems resides in their ability to entrap and solubilize hydrophobic drugs in the hydrophobic core. Such entrapment is easily carried out in a number of ways. Thus, the drug can be added to the aqueous solution containing micelles and incorporated by simple stirring, by heating to moderate temperatures, or by ultrasonication. The micelles are efficient carriers for a variety of hydrophobic or insoluble active agents, and are particularly suitable as carriers for anticancer agents, which will accumulate in the tumor by an endocytotic process.

While any of the anticancer agents that can form micellar complexes are suitable for this use, anticancer agents that are particularly suitable for micellar tumor targeting are those with low water solubility or high aromatic content, such as the anthracycline antibiotics (e.g. doxorubicin, daunorubicin, and epirubicin), mitomycin C, paclitaxel and its analogs (e.g. docetaxol), platinum analogs (e.g. cisplatin and carboplatin), and the like. Other agents may include anticancer proteins, such as neocarzinostatin, L-asparaginase, and the like, and photosensitizers used in photodynamic therapy.

In another aspect, there is provided a pharmaceutical composition according to each of the above, where the active agent is optionally further comprising one or more nutritional or dietary supplement. In one variation, the pharmaceutical composition according to each of the above wherein the active agent is one or more nutritional or dietary supplement. In another variation of the above pharmaceutical composition, the nutritional or dietary supplement is a vitamin The nutritional or dietary supplement composition described above may be used for administration to humans or other animals that strengthens and promotes retinal health through the prevention, stabilization, reversal and/or treatment of visual acuity loss in people with particular ocular diseases. The composition may also be administered to prevent, stabilize, reverse and/or treat cataract development. The present nutritional or dietary supplement composition described above may comprise of an effective amount of specific antioxidants and high-dosage zinc to decrease visual acuity loss. Visual acuity loss is decreased through the use of the above composition by reducing the risk of developing late stage or advanced age-related macular degeneration in persons with early age-related macular degeneration. The above composition may likewise reduce the risk of visual acuity loss associated with the development of cataracts. The application for the above composition is disclosed in U.S. Pat. No. 6,660, 297, the disclosure of which is incorporated herein in its entirety.

Ocular/Ophthalmic Applications:

The composition of the copolymer of the present invention described above may be used for the treatment of damage to the retina or the optic nerve of a subject. Such damage to the retina may be the result of macular degeneration, and such damage to the optic nerve may be the result of glaucoma.

The present invention provides methods and copolymer compositions described above for preventing and/or treating damage to the retina and optic nerve, including damage resulting from ischemic or hypoxic stress, excess intraocular pressure, or injury. The composition can be used specifically to treat damage associated with vascular occlusion or anterior ischemic optic neuropathy. The composition is also useful for treating damage arising from the presence of cytotoxins or neurotoxins, such as glutamate or other excitatory amino acids or peptides, excess intracellular calcium, and free radicals. In particular, the composition can be useful in treating damage associated with branch and central vein/artery occlusion, trauma, edema, angle-closure glaucoma, open-angle glaucoma, age related macular degeneration, retinitis pigmentosa, retinal detachments, damage associated with laser therapy, and surgical light-induced iatrogenic retinopathy.

The copolymer composition of the present invention may be employed in ocular delivery or ocular therapy for the treatment of ocular damage or disease. The composition may comprise of active agents, including for example, cAMP modulator, forskolin, adenylate cyclase activators, macrophage-derived factors that stimulate cAMP, macrophage activators, calcium ionophores, membrane depolarization, phosphodiesterase inhibitors, specific phosphodiesterase IV inhibitors, β2-adrenoreceptor inhibitors or vasoactive intestinal peptide, and including active agents such as neurotrophic factors including oncomodulin.

In one aspect, the composition of the present invention may be administered topically or by way of intraocular injection to the eye of the subject.

Bioerodible Graft Copolymer Matrix for Controlled Drug Delivery

To use the copolymer as a sustained-release vehicle, the active agent must be incorporated into a matrix of the copolymer or encapsulated within a capsule (or a "microcapsule" or "nanocapsule", as those terms are sometimes used) of the copolymer. Methods for the preparation of sustained-release dosage forms using biodegradable polymers are well known in the art, as discussed in the references cited in the "BACKGROUND OF THE INVENTION" section of this application, and in other references familiar to those of ordinary skill in the art; so that a person of ordinary skill in the art would have no difficulty, having regard to that skill and this disclosure, in preparing sustained-release formulations using the copolymer of this invention. Suitable active agents include therapeutic agents such as pharmaceutical or pharmacological active agents, e.g. drugs and medicaments, as well as prophylactic agents, diagnostic agents, and other chemicals or materials useful in preventing or treating disease. The compositions of this invention are particularly useful for the therapeutic treatment of humans and other mammals, but may also be used for other animals. In addition, the sustained-release compositions of this invention may also be used for the release of cosmetic and agricultural agents, or for the release of biocides, such as fungicides or other pesticides, into an environment where prolonged release of the active agent is desired.

In the case of matrix formulations, the copolymer is first mixed with the active agent. High homogeneity may be achieved by mixing the polymer in its heat softened state with the active agent, followed by lowering the temperature to harden the composition. Alternatively, the copolymer can be dissolved in an appropriate casting solvent, such as tetrahydrofuran, methylene chloride, chloroform or ethyl acetate, and the active agent can then be dispersed or dissolved in the copolymer solution, followed by evaporating the solvent to achieve the finished composition. Another method is grinding a solid copolymer material into powder which is then mixed with a powdered active agent. The active agent may also be incorporated into the mixture of monomers before polymerization provided that it is stable under the polymerization conditions and does not interfere with the polymerization reaction.

An alternate method for the incorporation and release of sensitive therapeutic agents is to use bioerodible copolymers that have physical properties tailored for this incorporation. The polymer composition may also be injected by syringe subcutaneously or intramuscularly as particles of 0.1 µm to 1000 µm, preferably 0.5 µm to 200 µm, and more preferably 1 µm to 150 µm suspended in a pharmaceutically acceptable injection base. Liquid vehicles useful for suspending the drug-copolymer composition for injection include isotonic saline solution or oils (such as corn oil, cottonseed oil, peanut oil and sesame oil) which, if desired, may contain other adjuvants.

Another injectable dosage form may be prepared from an active agent mixed in with a copolymer of the present invention. Such a dosage form may be administered by injection with or without a solvent.

The copolymer composition administered by either injection or implantation undergoes bioerosion in the body into non-toxic and non-reactive materials. By controlling the number of hydrolyzable bonds in the polymer, the active agent may be released at a desired rate. Implants prepared from the present copolymers in which the copolymer constitutes the matrix containing an active agent also have the advantage that they do not require removal because of the bioerodibility of the copolymer.

In some cases, particles with cores of the pure active agent coated with various thicknesses of the present copolymer may be preferred for sustained delivery of the active agent. Coating or encapsulation of discrete particles of the active agent may be accomplished by conventional methods which are all well-known to the person skilled in the art. For example, finely divided drug particles may be suspended in a solvent system (in which the drug is not soluble) containing the dissolved copolymer and other excipients, followed by spray drying. Alternatively, the drug particles may be placed in a rotating pan or a fluid-bed dryer and the copolymer dissolved in a carrier solvent is sprayed onto the drug particles until a suitable coating quantity is deposited on the particles to give a desired thickness. The coating may also be achieved by suspending the drug particles in a solvent system containing the dissolved copolymer followed by adding to the suspension a non-solvent causing the copolymer to precipitate and form a coating over the drug particles.

For the sustained release compositions, because the active agent will be released over a controlled period of time, the agent usually is present in an amount which is greater than the conventional single dose. The relative proportions of the active agent and the copolymer can vary over a wide range (e.g., 0.1 to 50 weight percent) depending on the therapeutic agent and the desired effect.

Sustained compositions of cosmetic and agricultural agents may also be prepared by any one of the methods as described above, using the copolymers of the present invention.

The solid copolymers are also useful for a variety of orthopedic applications. For example, they can be used as fracture fixation devices for repair of osteochondral defects, ligament and tendon reconstructions and bone substitutes. In addition, the fact that the present copolymers permit simultaneous selection of both a desired level of their mechano-physical state and a desired rate of bioerodibility, also renders them attractive as grafts or scaffolds on which cells can be cultured in vitro prior to implantation to regenerate tissues. Tissues which can be regenerated using this approach include but are not limited to bone, tendon, cartilage, ligaments, liver, intestine, ureter and skin tissues. For example, the copolymers may be used to regenerate skin for patients with burns or skin ulcers. Cartilages may be repaired by first isolating chondrocytes from a patient (or a donor), allowing them to proliferate on the scaffolds prepared from the present copolymer and re-implanting the cells in the patient.

The copolymer scaffolds or implants may further contain other biologically active substances or synthetic inorganic materials such as reinforcing filler material for enhancing the mechanical properties of the scaffolds or implants (e.g. calcium sodium metaphosphate fibers), antibiotics, or bone growth factors to induce and/or promote orthopedic restoration and tissue regeneration.

It is also understood that while not required, other pharmaceutically acceptable inert agents such as coloring agents and preservatives may also be incorporated into the composition.

Preferably the formulation is easily syringable or injectable, meaning that it can readily be dispensed from a conventional tube of the kind well known for topical or ophthalmic formulations, from a needleless syringe, or from a syringe with an 16 gauge or smaller needle (such as 16-25 gauge), and injected subcutaneously, intradermally or intramuscularly. The formulation may be applied using various methods known in the art, including by syringe, injectable or tube dispenser, for example, directly or indirectly to the skin or a wound.

After topical application or administration by injection, or any other routes of administration, including surface or subcutaneous application to open wounds, the active agent is released from the composition in a sustained and controlled manner. The rate of release may be regulated or controlled in a variety of ways to accommodate the desired therapeutic effect. The rate may be increased or decreased by altering the mole percentage of the α-hydroxy acid containing units or acid labile units in the poly(ortho ester)-polyethyleneglycol.

The compositions are also stable. The release rates of the active agent are not affected by irradiation for sterilization.

Particular Compositions and their Uses

Exemplary compositions of this invention, and their uses, include:
(1) compositions containing local anesthetics, optionally in combination with glucocorticosteroids such as dexamethasone, cortisone, hydrocortisone, prednisone, prednisolone, beclomethasone, betamethasone, flunisolide, fluocinolone acetonide, fluocinonide, triamcinolone, including deposition of the composition into surgical sites, and the like, for the prolonged relief of local pain or a prolonged nerve blockade. This use is discussed further below;
(2) compositions containing cancer chemotherapeutic agents, such as those listed above under "Active Agents", for deposition by syringe or by injection into tumors or operative sites from which a tumor has been ablated, for tumor control or treatment and/or the suppression of regrowth of the tumor from residual tumor cells after ablation of the tumor;
(3) compositions containing progestogens, such as flurogestone, medroxyprogesterone, norgestrel, norgestimate, norethindrone, and the like, for estrus synchronization or contraception;
(4) compositions containing antimetabolites such as fluorouracil and the like, as an adjunct to glaucoma filtering surgery; compositions containing antiangiogenic agents such as combrestatin, for the treatment of macular degeneration and retinal angiogenesis; and other compositions for the controlled release of ophthalmic drugs to the eye;
(5) compositions containing therapeutic polypeptides (proteins), such as insulin, LHRH antagonists, and the like, for the controlled delivery of these polypeptides, avoiding the need for daily or other frequent injection;
(6) compositions containing anti-inflammatory agents such as the NSAIDs, e.g. ibuprofen, naproxen, COX-1 or COX-2 inhibitors, and the like, or glucocorticosteroids, for intra-articular application or injection;
(7) compositions containing antibiotics, for the prevention or treatment of infection, especially for deposition into surgical sites to suppress post-operative infection, or into or on wounds, for the suppression of infection (e.g. from foreign bodies in the wound);
(8) compositions containing morphogenic proteins such as bone morphogenic protein;
(9) compositions containing RNA, DNA or other polynucleotides, such as antisense oligonucleotides;
(10) compositions containing antiemetic agents;
(11) compositions containing antigens in vaccines; and
(12) compositions comprising a combination of two or more of the above active agents for concurrent therapeutic applications.

Delivery of Controlled-Release Antiemetic Agents

The present invention further relates to a method for the treatment or prevention of emesis in a patient which comprises administering an 5-$HT_3$ antagonist, wherein the 5-$HT_3$ antagonist minimize the side effects of nausea and/or emesis associated with other pharmacological agents.

In a further aspect of the present invention, there is provided a pharmaceutical composition for the treatment or prevention of emesis comprising an $HT_3$ antagonist, optionally together with at least one pharmaceutically acceptable carrier.

As used herein, the term "emesis" include nausea and vomiting. The $HT_3$ antagonists in the injectable form of the present invention are beneficial in the therapy of acute, delayed or anticipatory emesis, including emesis induced by chemotherapy, radiation, toxins, viral or bacterial infections, pregnancy, vestibular disorders (e.g. motion sickness, vertigo, dizziness and Meniere's disease), surgery, migraine, and variations in intracranial pressure. The $HT_3$ antagonist of use in the invention are of particular benefit in the therapy of emesis induced by radiation, for example during the treatment of cancer, or radiation sickness; and in the treatment of post-operative nausea and vomiting. The HT3 antagonists in the injectable form of the invention are beneficial in the therapy of emesis induced by antineoplastic (cytotoxic) agents including those routinely used in cancer chemotherapy, and emesis induced by other pharmacological agents, for example, alpha-2 adrenoceptor antagonists, such as yohimbine, MK-912 and MK-467, and type IV cyclic nucleotide phosphodiesterase (PDE4) inhibitors, such as RS14203, CT-2450 and rolipram.

Particular examples of chemotherapeutic agents are described, for example, by D. J. Stewart in *Nausea and Vomiting. Recent Research and Clinical Advances*, ed. J. Kucharczyk et al., CRC Press Inc., Boca Raton, Fla., USA, 1991, pages 177-203, see page 188. Examples of commonly used chemotherapeutic agents include cisplatin, dacarbazine (DTIC), dactinomycin, mechlorethamine (nitrogen mustard), streptozocin, cyclophosphamide, carmustine (BCNU), lomustine (CCNU), doxorubicin (adriamycin), daunorubicin, procarbazine, mitomycin, cytarabine, etoposide, methotrexate, 5-fluorouracil, vinblastine, vincristine, bleomycin and chlorambucil (see R. J. Gralle et al. in *Cancer Treatment Reports*, 1984, 68, 163-172).

Many of the antiemetic agents are conventionally used in the form of their acid addition salts, as this provides solubility in aqueous injection media. However, because the presence of the large amount of acid within such a local antiemetic acid addition salt will result in more rapid degradation of the composition and rapid release of the antiemetic agent, it is generally desirable to use the antiemetic agent in the free base form. Alternatively, the antiemetic may be used with only a small proportion of the acid addition salt present (addition of small quantities of the acid addition salt may provide enhanced release if desired).

The injectable form of an antiemetic agent of the present invention is prepared by incorporating the antiemetic agent into the delivery vehicle in a manner as described above. The concentration of the antiemetic agent may vary from about 0.1-80 wt. %, preferably from about 0.2-60 wt. %, more preferably 0.5-40 wt. %, most preferably from about 1-5 wt %, for example, about 2-3 wt. %. The composition is then filled into a syringe with a 16-25 gauge needle, and injected into sites that have been determined to be most effective. The copolymer injectable composition of the present invention can be used for controlled delivery of both slightly soluble and soluble antiemetic agents.

Suitable classes of antiemetic agents employed in the present invention include, for example, a 5-$HT_3$ antagonist such as ondansetron, granisetron or tropisetron; a dopamine antagonist such as metoclopramide or domperidone; an anticholinergic agent such as scopolamine; a $GABA_B$ receptor agonist such as baclofen; an $NK_1$ receptor antagonist as described, for example, in WO 97/49710; or a $GABA_A\alpha_2$ and/or $\alpha_3$ receptor agonist as described in WO 99/67245.

The $5\text{-}HT_3$ antagonists employed in the present invention are also useful for the treatment of or prevention of emesis in conjunction with the use of other antiemetic agents known in the art.

In one particular aspect, suitable classes of other antiemetic agents of use in conjunction with the present invention include, for example, alpha-2 adrenoreceptor agonists including for example, clonidine, apraclonidine, para-aminoclonidine, brimonidine, naphazoline, oxymetazoline, tetrahydrozoline, tramazoline, detomidine, medetomidine, dexmedetomidine, B-HT 920, B-HIT 933, xylazine, rilmenidine, guanabenz, guanfacine, labetalol, phenylephrine, mephentermine, metaraminol, methoxamine and xylazine.

As noted, the compounds or agents employed in the present invention are also useful for the treatment of or prevention of emesis in conjunction with another antiemetic agents known in the art, such as a $5\text{-}HT_3$ antagonist, a dopamine antagonist, an anticholinergic agent, a $GABA_B$ receptor agonist, an $NK_1$ receptor antagonist, and a $GABA_A\alpha_2$ and/or $\alpha 3$ receptor agonist.

In another aspect of the invention, the antiemetic agents as a single agent or as a combination, may be used independently in the form of a salt or salts or mixtures of the agent and the salt of the agent. Suitable pharmaceutically acceptable salts of the compounds of use in the present invention include acid addition salts which may, for example, be formed by mixing a solution of the compound with a solution of a pharmaceutically acceptable non-toxic acid such as hydrochloric acid, iodic acid, fumaric acid, maleic acid, succinic acid, acetic acid, citric acid, tartaric acid, carbonic acid, phosphoric acid, sulfuric acid and the like. Salts of amine groups may also comprise the quaternary ammonium salts in which the amino nitrogen atom carries an alkyl, alkenyl, alkynyl or aralkyl group. Where the compound carries an acidic group, for example a carboxylic acid group, the present invention also contemplates salts thereof, preferably non-toxic pharmaceutically acceptable salts thereof, such as the sodium, potassium and calcium salts thereof.

It will be appreciated that when using a combination of the present invention, the $5\text{-}HT_3$ antagonists and the other antiemetic agent will be administered to a patient together in the copolymer injectable form of the invention. In one aspect of the invention, the compounds may be in the same pharmaceutically acceptable carrier and therefore administered simultaneously.

When administered in combination, either as a single product in the copolymer injectable form or as separate pharmaceutical compositions, the $5\text{-}HT_3$ antagonists and the other antiemetic medicament are to be presented in a ratio which is consistent with the manifestation of the desired effect. In particular, the ratio by weight of the $5\text{-}HT_3$ antagonists and the other antiemetic agent will suitably be between 0.001 to 1 and 1000 to 1, and especially between 0.01 to 1 and 100 to 1.

The present invention is further directed to a method for ameliorating the symptoms attendant to emesis in a patient comprising administering to the patient an $5\text{-}HT_3$ antagonists. In accordance with the present invention the $5\text{-}HT_3$ antagonists is administered to a patient in a quantity sufficient to treat or prevent the symptoms and/or underlying etiology associated with emesis in the patient.

Delivery of Controlled-Release Local Anesthetics by Injection

Local anesthetics induce a temporary nerve conduction block and provide pain relief which lasts from a few minutes to a few hours. They are frequently used to prevent pain in surgical procedures, dental manipulations or injuries.

The synthetic local anesthetics may be divided into two groups: the slightly soluble compounds and the soluble compounds. Conventionally, the soluble local anesthetics can be applied topically and by injection, and the slightly soluble local anesthetics are used only for surface application. The local anesthetics conventionally administered by injection can also be divided into two groups, esters and non-esters. The esters include (1) benzoic acid esters (piperocaine, meprylcaine and isobucaine); (2) para-aminobenzoic acid esters (procaine, tetracaine, butethamine, propoxycaine, chloroprocaine); (3) meta-aminobenzoic acid esters (metabutethamine, primacaine); and (4) para-ethoxybenzoic acid ester (parethoxycaine). The non-esters are anilides (amides or nonesters) which include bupivacaine, lidocaine, mepivacaine, pyrrocaine and prilocaine.

Many of the local anesthetics are conventionally used in the form of their acid addition salts, as this provides solubility in aqueous injection media. However, because the presence of the large amount of acid within such a local anesthetic acid addition salt will result in more rapid degradation of the poly(ortho ester)-polyethyleneglycols and release of the local anesthetic, it is generally desirable to use the local anesthetics in free base form, or with only a small proportion of the acid addition salt present (addition of small quantities of the acid addition salt may provide enhanced release if desired).

The injectable form of a local anesthetic of the present invention is prepared by incorporating the local anesthetic into the delivery vehicle in a manner as described above. The concentration of the local anesthetic may vary from about 0.1-80 wt. %, preferably from about 1-60 wt. %, more preferably from about 0.5-40 wt. %, most preferably from about 1-5 wt. %, for example, about 2-3 wt. %. The composition is then filled into a syringe with a 16-25 gauge needle, and injected into sites that are painful or to be subjected to surgical procedures. The injectable composition of the present invention can be used for controlled delivery of both slightly soluble and soluble local anesthetics.

Because the duration of action of a local anesthetic is proportional to the time during which it is in actual contact with nervous tissues, the present injectable delivery system can maintain localization of the anesthetic at the nerve for an extended period of time which will greatly prolong the effect of the anesthetic.

A number of authors, including Berde et al., U.S. Pat. No. 6,046,187 and related patents, have suggested that the co-administration of a glucocorticosteroid may prolong or otherwise enhance the effect of local anesthetics, especially controlled-release local anesthetics; and formulations containing a local anesthetic and a glucocorticosteroid, and their uses for controlled release local anesthesia, are within the scope of this invention.

EXAMPLES

Preparation of Poly(Ortho Ester)-Polyethyleneglycols

The following syntheses illustrate the preparation of representative poly(ortho ester)-polyethyleneglycols. The starting materials are either commercially available or may be prepared as described in the preceding sections and in U.S. Pat. Nos. 4,549,010 and 5,968,543.

Preparation of the degradable polymers of the present invention may be illustrated with the general procedure described using an unfunctionalized diketene acetal and poly(ethylene glycol) (PEG) as the source of diol. However, it will be appreciated by those of ordinary skill in the art that other diols, including PEGs of lower or higher molecular weight, are also suitable for the practice of the invention.

The reaction of poly(ethylene glycol) (PEG's with molecular weights of 3,400 g/mol were used) and commercially available triethylene glycol di-vinyl ether. PEG is selected as the diol because it is generally recognized as safe (GRAS) by drug regulatory authorities and is widely used in pharmaceutical formulation. The use of the unfunctionalized diketene acetal, and triethylene glycol diketene acetal, in the preliminary experiments was conducted to confirm a suitable degradation profile (needed for lysosomal degradation) and to confirm in vitro biocompatibility. It will be understood by one of ordinary skill in the art that degradable poly(ortho ester)-polyethyleneglycols polymers of the invention may also be prepared from functionalized starting materials. For example, functionalized diketene acetals, may be used as starting materials in the preparation of the degradable poly(ortho ester)-polyethyleneglycols polymers of the invention. In each case m is an integer representing a PEG molecule of the identified molecular weight Mn.

The molecular weight ($M_n$ in GPC) of the poly(ortho ester) before PEG grafting vary from 2000-5000.

The starting materials were purified and prepared as follows:

1,4-cyclohexyldimethanol divinyl ether was purified by distillation over $CaH_2$.

1,4-cyclohexanedimethanol was purified by reprecipitation from ethylacetate.

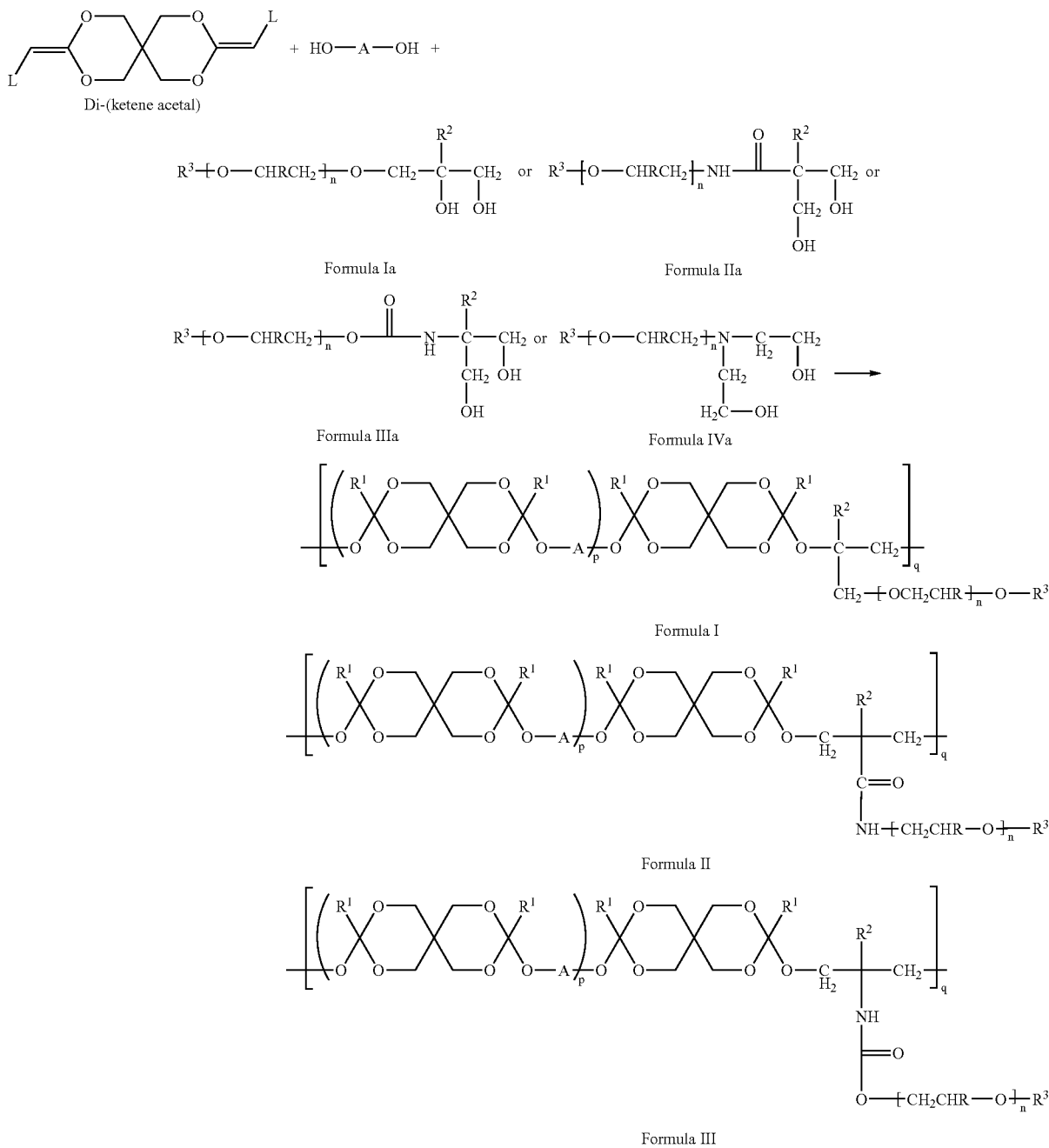

Scheme I: Synthesis of Polyethyleneglycol-Poly(orthoester) Graph Copolymers

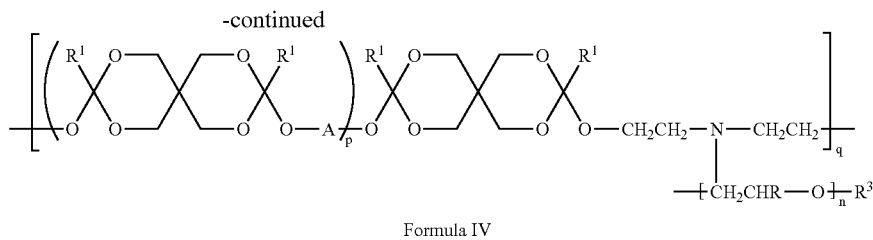

Formula IV

Fmoc-protected 2-amino-1,3-propanediol (Fmoc-protected serinol) was synthesized as follows: 2 g (0.022 mol) 2-amino-1,3-propanediol (serinol) were dissolved in 54 ml of 10% solution of Na2CO3. 10 ml dioxane were added and the mixture was stirred in an ice-bath. 7.38 g (0.0285 mol) of 9-fluorenylmethyl chloroformate (Fmoc-Cl) were dissolved in 25 ml dioxane and added dropwise the above solution. The reaction mixture was stirred at room temperature for 4 hrs. 200 ml of water were added and the product was extracted with ethylacetate. Ethylacetate layers were collected and dried over $MgSO_4$. After filtration and evaporation of the solvent, the product was reprecipitated from ethylacetate/hexane and dried under vacuum.

PEG-N-succinimidyl carbonate (PEG-SC) was prepared as follows: 1 mmol of α-methyl-ω-hydroxy polyethylene glycol (MPEG-OH) was dissolved in 2 ml acetonitrile and 0.4 ml pyridine. 2 mmol of N,N'-disuccinimidyl carbonate were added to the solution and the mixture was stirred at room temperature overnight. The solution was precipitated in ether, the precipitate was filtered and dried under vacuum.

Preparation of Pharmaceutical Compositions

Thermogel pharmaceutical compositions with bupivacaine as the active agent were prepared by first milling the bupivacaine into fine particles and sieving, before mixing with selected amounts of a poly(ortho ester)-polyethyleneglycol. The mixing process was performed at room temperature under vacuum. Further size reduction of the bupivacaine particles was carried out by passing the thermogel composition through a ball mill.

Thermogel pharmaceutical compositions with granisetron as the active agent are prepared by first milling the bupivacaine into fine particles and sieving, before mixing with selected amounts of a poly(ortho ester)-polyethyleneglycol. The mixing process is performed at room temperature under vacuum. Further size reduction of the granisetron particles is carried out by passing the thermogel composition through a ball mill.

Release Profiles of the Pharmaceutical Compositions

The compositions of the example above were weighed, placed into bottles with screw caps. 100 mL of 50 mM PBS (pH 7.4) was added to each bottle. The test bottles were transferred to a 37° C. incubator and placed on top of a rotor shaker (36 rpm). At various time points, bottles were removed from the incubator and samples of about 5 mL were removed and analyzed for bupivacaine content by HPLC at 263 nm. The remaining volume of buffer was removed and replaced with 100 mL fresh buffer.

Depending on the compositions, certain composition provides release rates that are slower or faster than others. These test results demonstrates that the pharmaceutical compositions of the present invention have the advantage that the release rates of the composition may be adjusted and controlled in a variety of ways. The rates of release can be adjusted to accommodate a desired therapeutic effect by either altering the mole percentage of the α-hydroxyacid containing units in the polyorthoester as disclosed in U.S. Pat. No. 5,968,543.

The compositions can be irradiated, and the release rate of some compositions before and after irradiation shows no significant difference over twelve days using the test described above.

The foregoing is offered primarily for purposes of illustration. It will be readily apparent to those skilled in the art that the molecular structures, proportions of the various components in the delivery vehicle or pharmaceutical composition, method of manufacture and other parameters of the invention described herein may be further modified or substituted in various ways without departing from the spirit and scope of the invention. For example, effective dosages other than the particular dosages as set forth herein above may be applicable as a consequence of variations in the responsiveness of the mammal being treated for any of the indications with the compounds of the invention indicated above. Likewise, the specific pharmacological responses observed may vary according to and depending upon the particular active compounds selected or whether there are present pharmaceutical carriers, as well as the type of formulation and mode of administration employed, and such expected variations or differences in the results are contemplated in accordance with the objects and practices of the present invention. It is intended, therefore, that the invention be defined by the scope of the claims which follow and that such claims be interpreted as broadly as is reasonable.

DIOL FOR FORMULA I

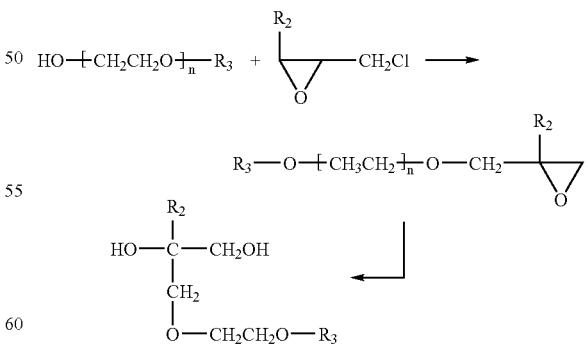

DIOL FOR FORMULA II

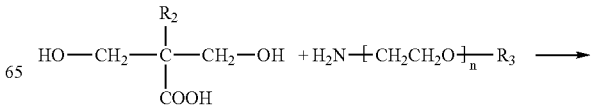

-continued

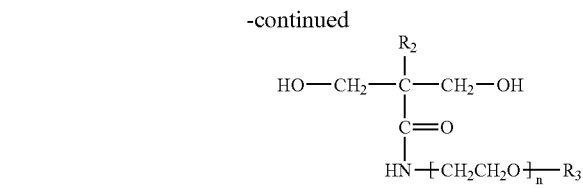

DIOL FOR FORMULA III

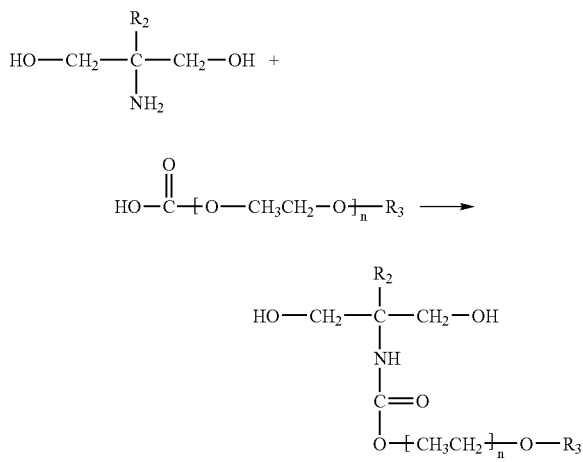

DIOL FOR FORMULA IV

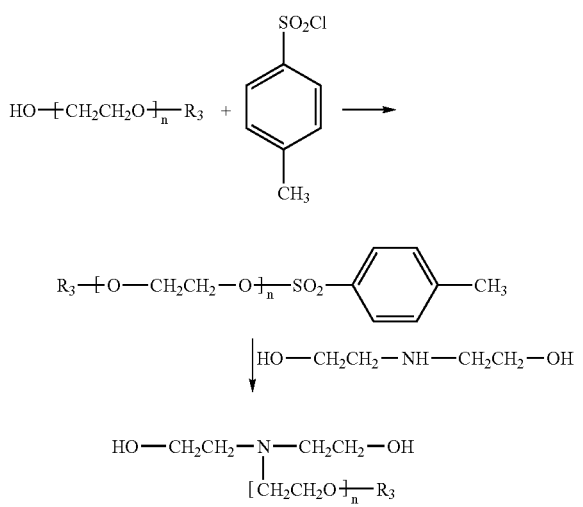

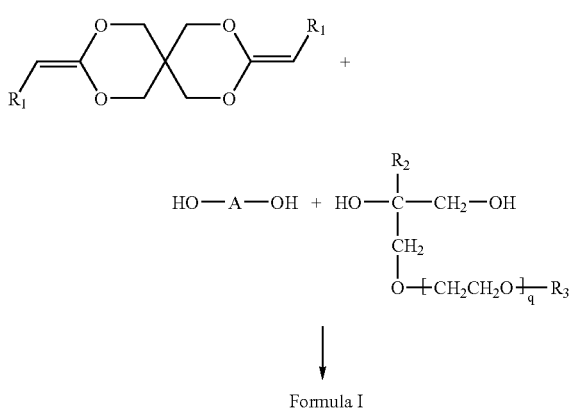

Formula I

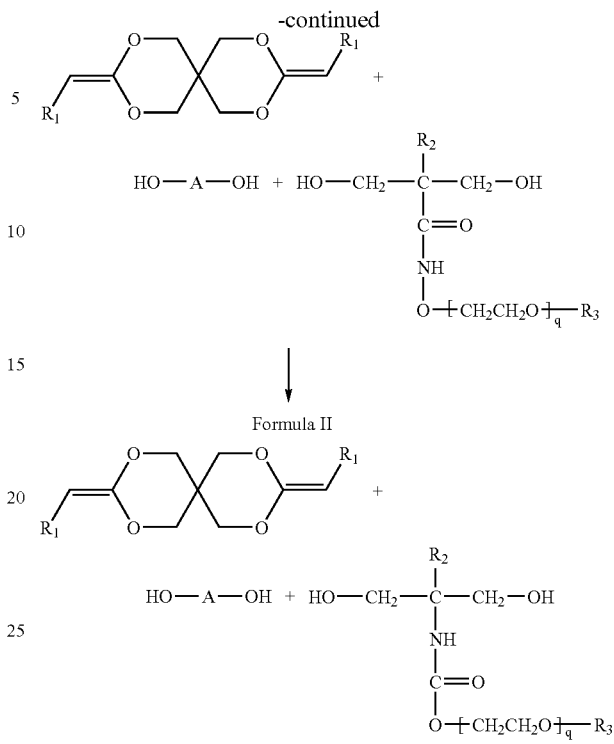

Formula IV

Epoxy-terminated methoxy-poly(ethylene glycol): A flask was charged with two moles of epichlorohydrin, and three moles of sodium hydroxide were added to the reaction vessel with stirring. One mole of methoxy-poly(ethylene glycol), (MPEG 2000) was added dropwise, keeping the reaction temperature at around 40° C. After addition of MPEG, stirring was continued for 1.5 h. The reaction mixture was filtered to remove excess sodium hydroxide and formed sodium chloride, and then dried over molecular sieves.

Hydrolysis of epoxy-terminated methoxy-poly(ethylene glycol): 240 grams of the epoxy-terminated methoxy-poly (ethylene glycol) was dissolved in 1500 of water and 0.2 ml concentrated sulfuric acid added. The mixture was stirred vigorously at room temperature for 8 h, the acid neutralized with sodium hydroxide and the water distilled off under reduced pressure. The product was carefully dried to remove all traces of water and used in the preparation of the graft copolymer without further purification.

Preparation of Graft Copolymer: The reaction was carried out in a dry-box. 21 g (0.1 mole) of 3,9-diethylidene-2,4,8, 10-tetraoxaspiro[5.5]undecane, 16.8 g (0.08 mole) of cyclohexanedimethanol and 41.5 g (0.02 mole) of diol I (R=H)

were dissolved in 120 ml of tetrahydrofuran in a round bottom flask, and 7.14 ml p-toluene sulfonic acid (2% solution in tetrahydrofuran) were added under stirring and the reaction carried out for 4 h.

The flask was removed from the dry-box and several drops of diisopropyl ethylamine added to neutralize the acidic catalyst. The polymer was slowly added to a large excess of methanol, and the solid product isolated by filtration.

Other poly(ortho ester)-polyethyleneglycols of the formulae disclosed herein, and/or those containing other diols of formulae HO—$R^4$—OH, HO—$R^5$—OH, HO—$R^6$—OH, and HO—$R^7$—OH, are prepared by similar methods.

What is claimed is:

1. A graft copolymer of Formula L2:

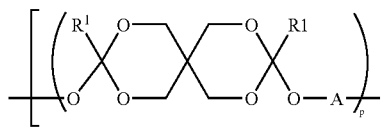

Formula L2

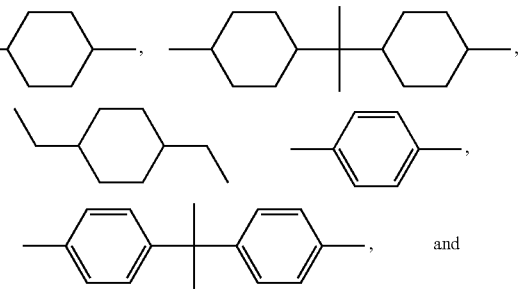

and

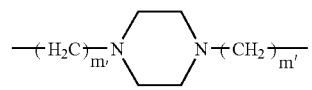

where m' is an integer from 1 to 6.

2. A graft copolymer of Formula III,

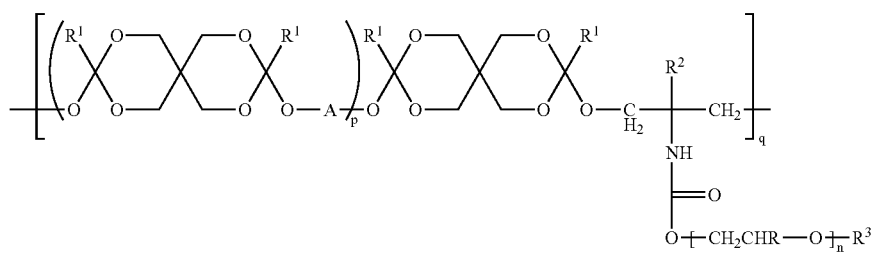

Formula III

-continued

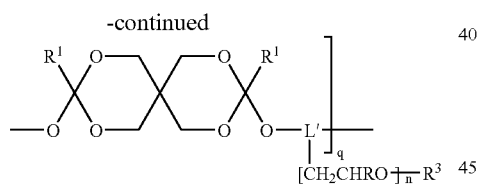

wherein:
L' is linker comprising the formula

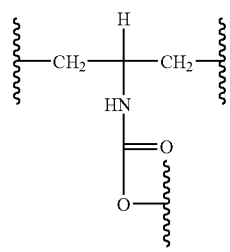

n is an integer from 2 to 500;
p and q are independently integers from 5 to 100;
$R^1$ is —$C_1$-$C_4$ alkyl;
R and $R^3$ are each independently H or $C_1$-$C_4$ alkyl; and
each A is $R^5$; where: $R^5$ is selected from:

wherein:
n is an integer from 2 to 500;
p and q are independently integers from 5 to 100;
$R^1$ is —$C_1$-$C_4$ alkyl;
R, $R^2$ and $R^3$ are each independently H or $C_1$-$C_4$ alkyl; and
each A is $R^5$ where:
$R^5$ is selected from:

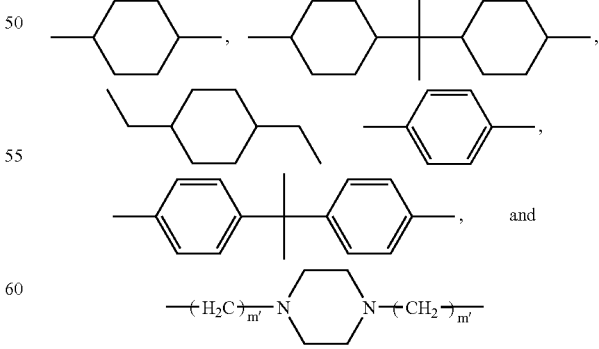

and

where m' is an integer from 1 to 6.

3. The copolymer of claim 2 which is a compound of Formula III where R is H.

4. The copolymer of claim 3 where $R^1$ is ethyl and $R^2$ is H.

5. The copolymer of claim 3 where is $R^5$ is 1,4-cyclohexanedimethylene.

6. The copolymer of claim 2 which is a compound of Formula III where R is H and $R^3$ is methyl.

7. The copolymer of claim 6 where $R^1$ is ethyl.

8. The copolymer of claim 6 where $R^5$ is 1,4-cyclohexanedimethylene.

* * * * *